(12) United States Patent
Koyakutty et al.

(10) Patent No.: US 9,707,186 B2
(45) Date of Patent: Jul. 18, 2017

(54) CORE-SHELL PARTICLE FORMULATION FOR DELIVERING MULTIPLE THERAPEUTIC AGENTS

(71) Applicants: Manzoor Koyakutty, Kochi (IN); Shantikumar Nair, Kochi (IN); Archana P. Retnakumari, Kochi (IN)

(72) Inventors: Manzoor Koyakutty, Kochi (IN); Shantikumar Nair, Kochi (IN); Archana P. Retnakumari, Kochi (IN)

(73) Assignee: AMRITA VISHWA VIDYAPEETHAM, Ponekkara (PO), Kochi (IN)

( * ) Notice: Subject to any disclaimer, the term of this patent is extended or adjusted under 35 U.S.C. 154(b) by 0 days.

(21) Appl. No.: 14/585,013

(22) Filed: Dec. 29, 2014

(65) Prior Publication Data
US 2015/0209288 A1  Jul. 30, 2015

Related U.S. Application Data

(63) Continuation-in-part of application No. PCT/IN2013/000141, filed on Mar. 12, 2013, and a continuation-in-part of application No. 14/465,521, filed on Aug. 21, 2014, now Pat. No. 9,402,918.

(Continued)

(51) Int. Cl.
| | | |
|---|---|---|
| A61K 9/51 | (2006.01) |
| A61K 47/48 | (2006.01) |
| A61K 9/00 | (2006.01) |
| A61K 31/506 | (2006.01) |
| A61K 31/436 | (2006.01) |
| A61K 31/44 | (2006.01) |
| A61K 31/713 | (2006.01) |
| A61K 45/06 | (2006.01) |
| A61K 38/40 | (2006.01) |
| A61K 39/44 | (2006.01) |

(Continued)

(52) U.S. Cl.
CPC .......... *A61K 9/5169* (2013.01); *A61K 9/0019* (2013.01); *A61K 31/436* (2013.01); *A61K 31/44* (2013.01); *A61K 31/506* (2013.01); *A61K 31/713* (2013.01); *A61K 45/06* (2013.01); *A61K 47/48284* (2013.01); *A61K 47/48315* (2013.01); *A61K 47/48884* (2013.01); *A61K 9/167* (2013.01); *A61K 38/00* (2013.01); *A61K 38/40* (2013.01); *A61K 39/44* (2013.01)

(58) Field of Classification Search
None
See application file for complete search history.

(56) References Cited

U.S. PATENT DOCUMENTS 6,713,083 B1 *  3/2004  McGregor ........... A61K 9/1652
                                                      264/5
2005/0037989 A1 *  2/2005  Lewis ................... C12N 15/111
                                                      514/44 A (Continued)

*Primary Examiner* — Bethany Barham
*Assistant Examiner* — Barbara Frazier

(57) ABSTRACT

A core-shell particle formulation for delivering multiple therapeutic agents is disclosed. More particularly, the formulation comprising protein-protein core-shell particle configured to independently release therapeutic agents from the core and the shell. Moreover, the core-shell particle bearing therapeutic agents enable treatment against the diseases such as cancer, inflammatory and auto-immune diseases.

8 Claims, 22 Drawing Sheets

Related U.S. Application Data which is a continuation of application No. PCT/IN2013/000008, filed on Feb. 19, 2013.

(51) Int. Cl.
*A61K 38/00* (2006.01)
*A61K 9/16* (2006.01)

(56) References Cited

U.S. PATENT DOCUMENTS

| | | | |
|---|---|---|---|
| 2007/0053845 A1* | 3/2007 | Sengupta | A61K 9/1271 424/46 |
| 2010/0112077 A1* | 5/2010 | Desai | A61K 9/0019 424/499 |

* cited by examiner

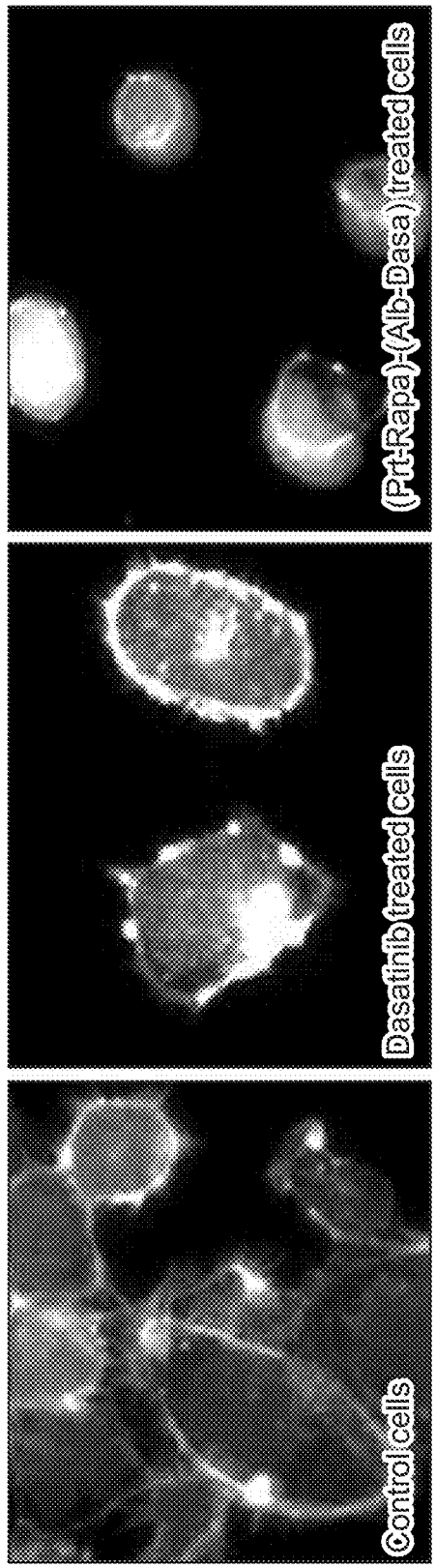

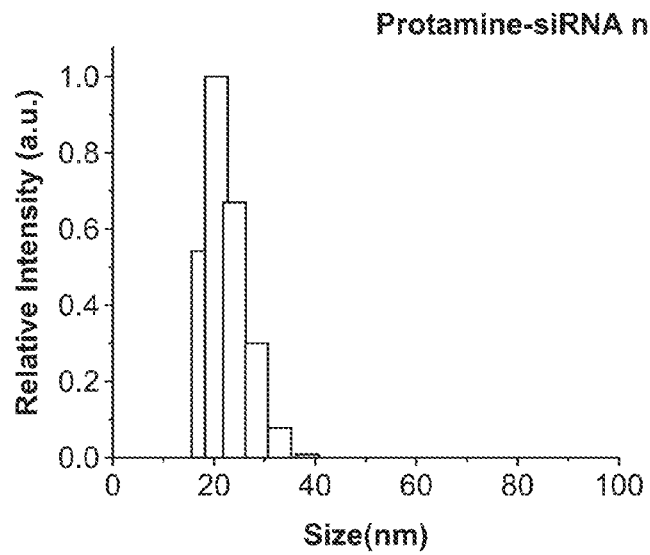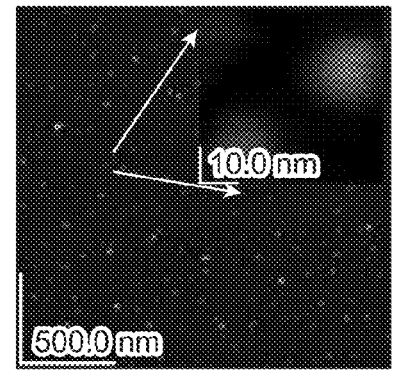
FIG. 13A          FIG. 13B
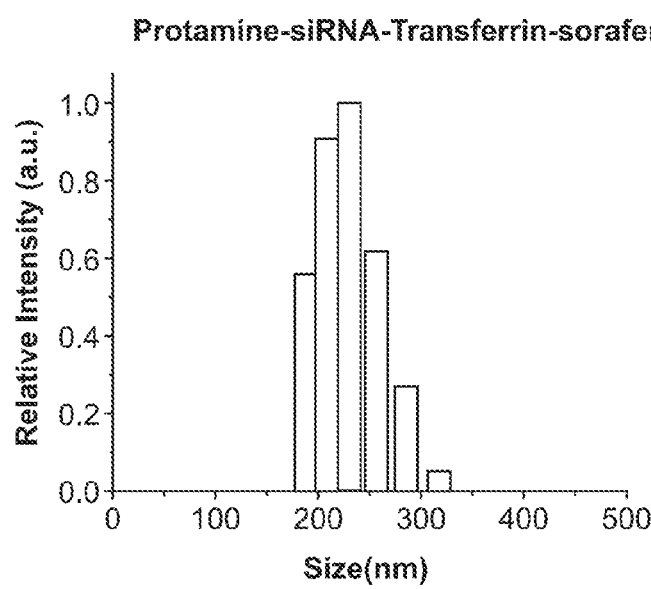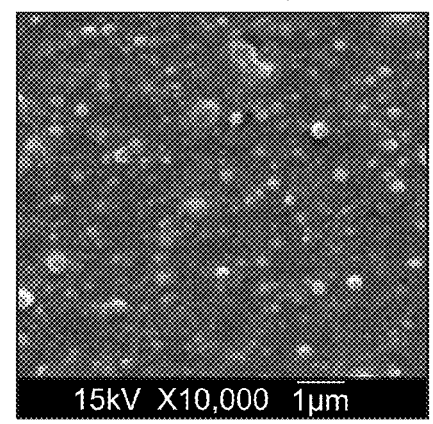
FIG. 13C          FIG. 13D

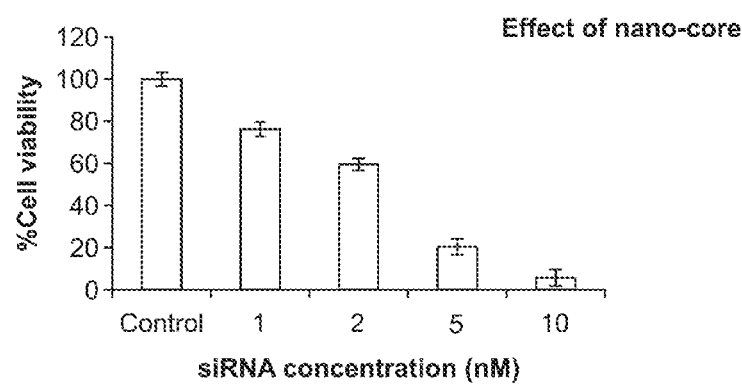
FIG. 15A
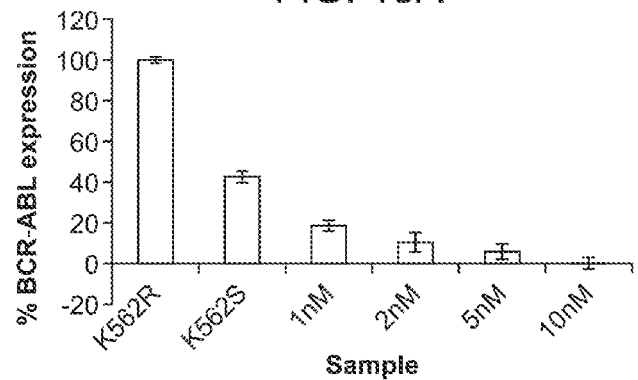 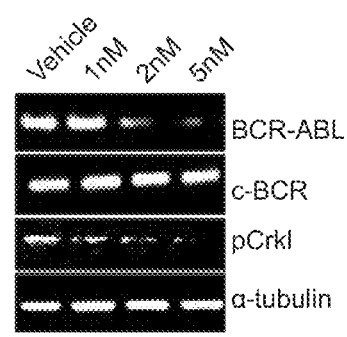
FIG. 15B  FIG. 15C

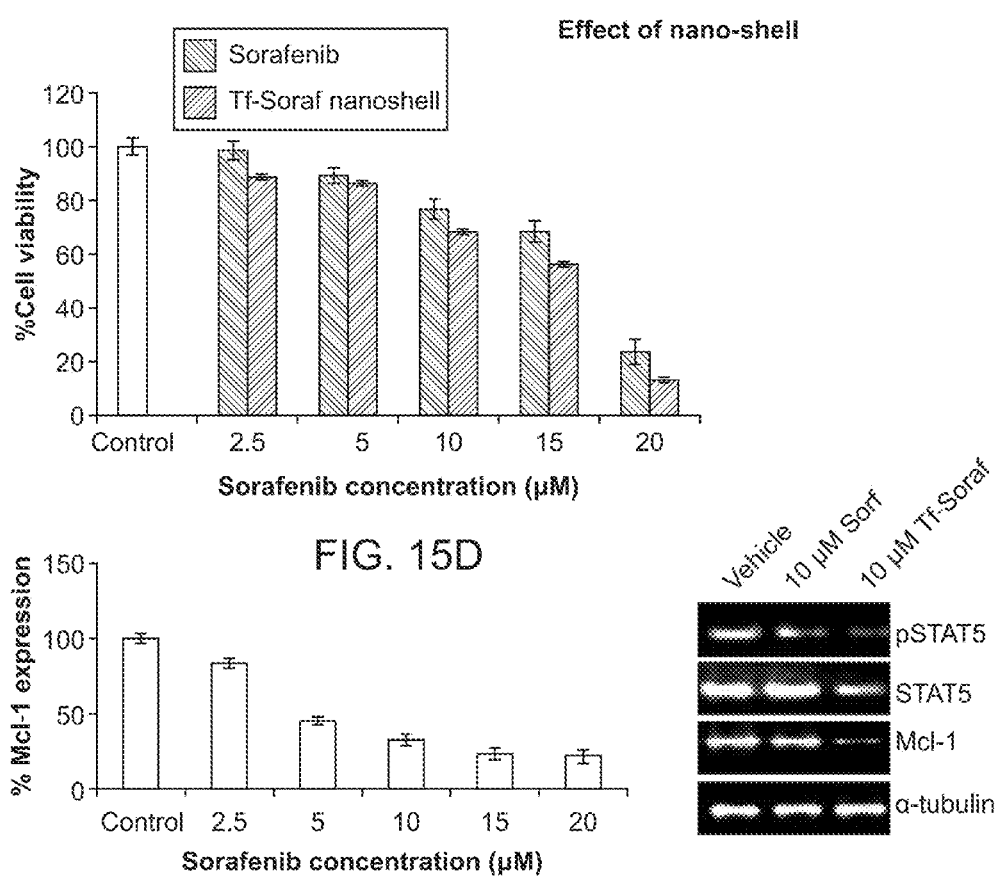

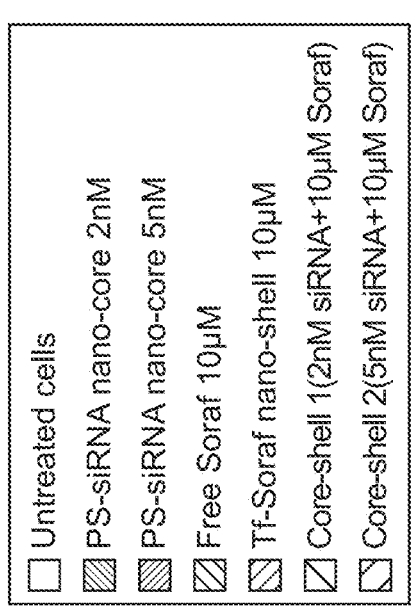
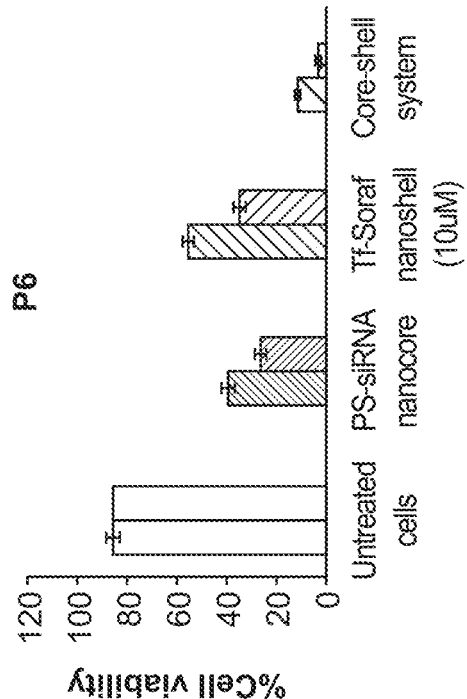
FIG. 16F
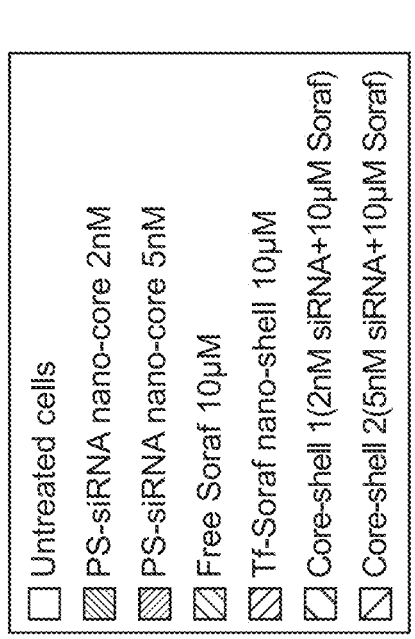
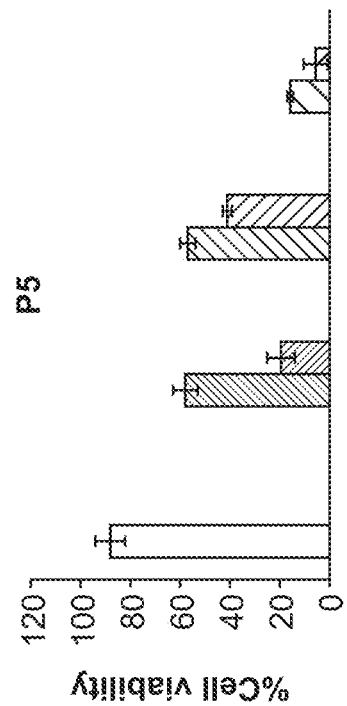
FIG. 16E

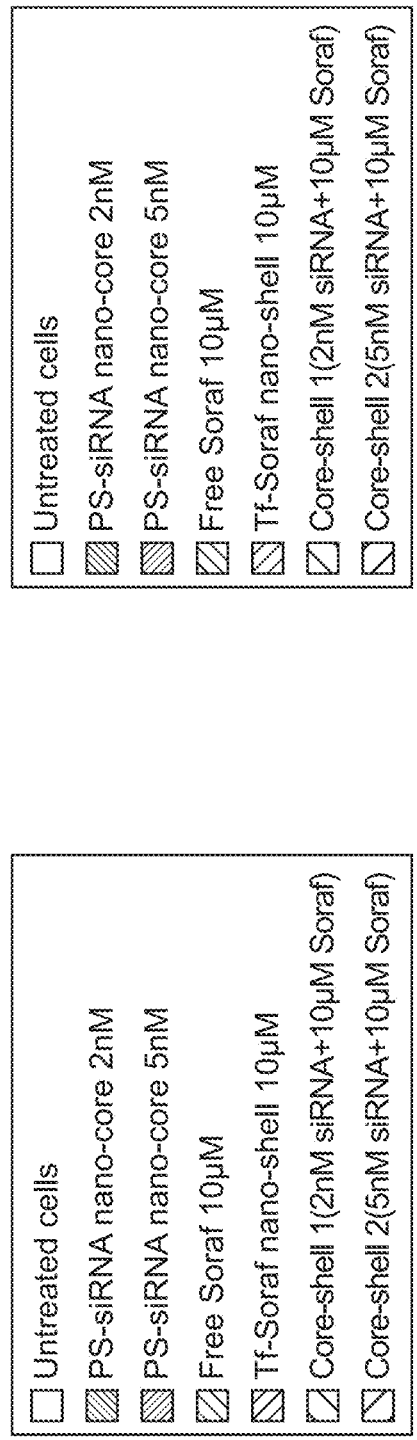
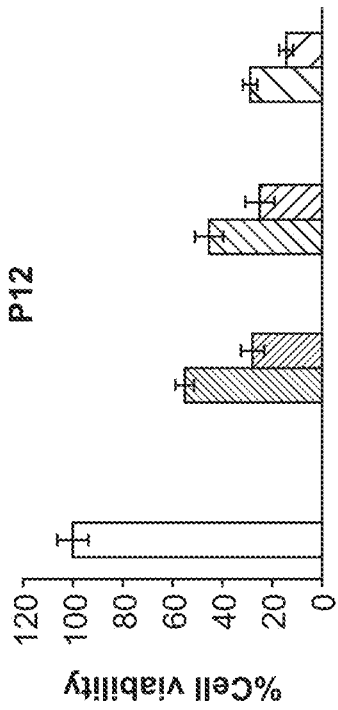
FIG. 16L
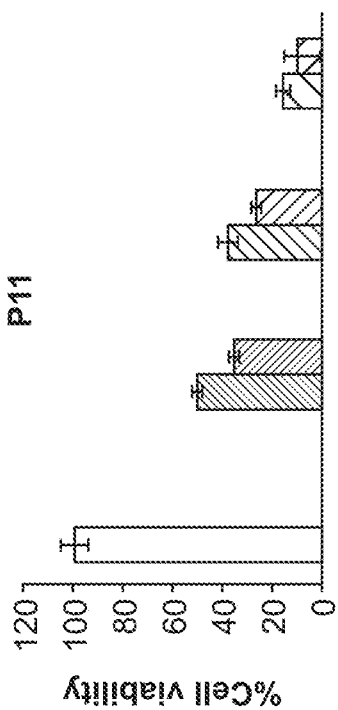
FIG. 16K

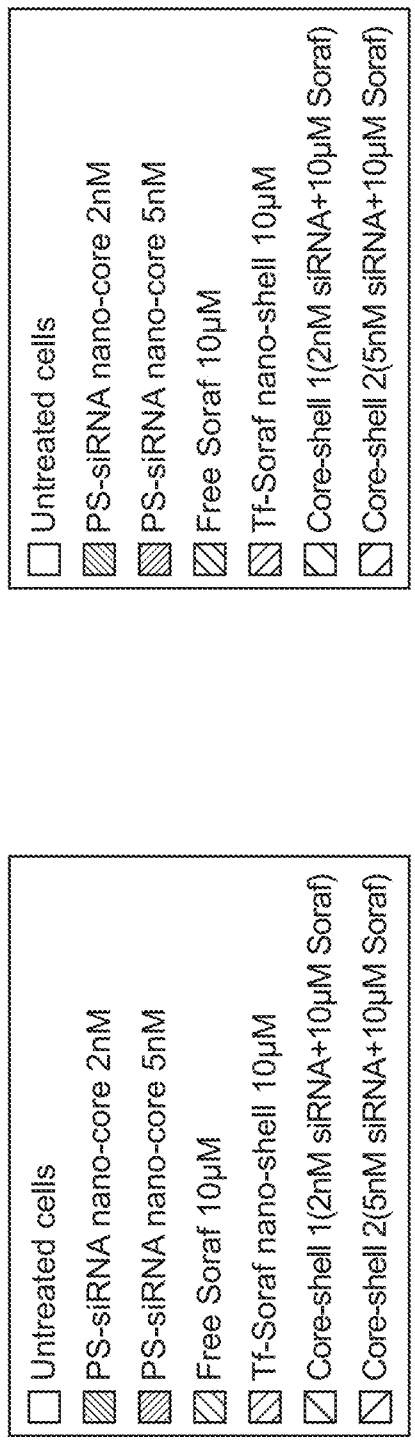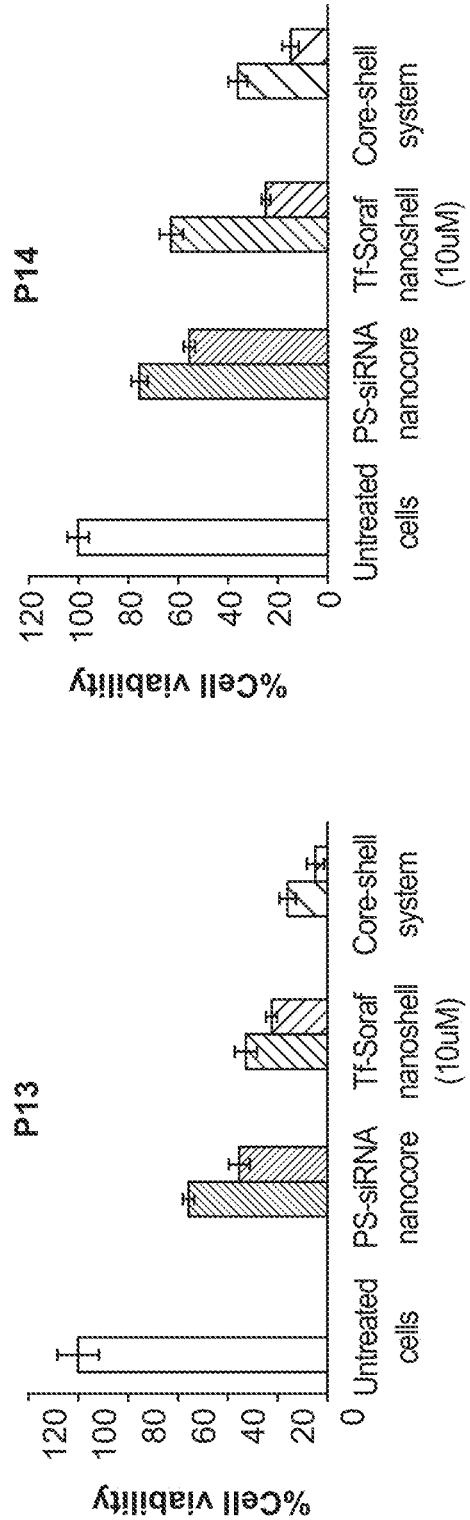
FIG. 16M
FIG. 16N

CORE-SHELL PARTICLE FORMULATION FOR DELIVERING MULTIPLE THERAPEUTIC AGENTS

CROSS-REFERENCES TO RELATED APPLICATIONS

This application is a continuation-in-part of PCT international application No. PCT/IN2013/000141 filed on Mar. 12, 2013, which claims priority to Indian patent application No. 2550/CHE/2012, filed on Jun. 27, 2012, and a continuation-in-part of U.S. application Ser. No. 14/465,521 filed on Aug. 21, 2014, which is a continuation of PCT international application No. PCT/IN2013/000108 filed on 19 Feb. 2013, which claims priority to Indian patent application No. 644/CHE/2012, filed on 21 Feb. 2012, the full disclosures of which are incorporated herein by reference.

FIELD OF THE INVENTION

This invention relates generally to core-shell particle formulations for delivering multiple therapeutic agents, and more particularly, core-shell particle formulation configured to independently release therapeutic agents from the core and the shell. The core-shell particle bearing therapeutic agents are envisaged to enable treatment against diseases such as cancer, inflammatory and auto-immune diseases.

DESCRIPTION OF THE RELATED ART

Successful management of diseases requires development of drug delivery systems with maximum therapeutic benefits. Most of the diseases including cancer are associated with deregulation of multiple signaling pathways. An essential requirement of drug delivery systems is the controlled delivery of a therapeutic molecule to the diseased site at therapeutically relevant concentrations. The site-specific delivery of multiple therapeutic molecules to the diseased site using a single carrier vehicle in a specified steady concentration for prescribed time duration improves the efficacy of the therapeutic molecule and thus reduces the possible side effects, thus improving the therapeutic index. The release kinetics of the therapeutic molecule is often dependent upon the encapsulating material/carrier properties, drug-particle interactions or through some other trigger mechanisms, which assist in the drug release. Design of drug delivery systems generally involves encapsulation of the drug within a suitable shell to form particles of suitable size. The drug can be distributed either within a hollow shell or within the solid particle.

The advantages of such encapsulation is the control over release kinetics, giving the ability for slow release over a long period of time, and protection of the drug from a potentially degrading biological environment. Recent advancements in nanotechnology have revolutionized the field of drug delivery. The advantages of nanoparticles over conventional systems of drug delivery include, high surface area to volume ratio enabling better cellular uptake, thereby affecting intracellular pathways of action compared to that of free molecules and the ability to efficiently bio-functionalize the particulate surface with cell-specific targeting ligands for specific attachment to particular cells which require drug action. Protein based drug delivery systems are ideal platforms for the delivery of multiple therapeutics for in vivo applications due to their amphiphilic nature, biocompatibility and biodegradability coupled with low toxicity. The degradation products of the carrier system will be amino acids, which are well tolerated by the human body.

Depending upon the nature of the molecules to be encapsulated, a wide choice of preparations is available such as desolvation, heat denaturation, coacervation, cross-linking, nano precipitation emulsification, etc. The particle size of the system can be fine-tuned with slight changes in synthesis parameters such as temperature, pH, etc. Moreover, the nanoparticles possess greater stability during storage or in vivo after administration, and provide surface functional groups for conjugation to cancer targeting ligands. They also are suitable for administration through different routes.

US20101122077 describes combination therapy methods of treating proliferative diseases like cancer with a first therapy comprising of effective amount of a taxane in a nanoparticle composition, with second therapy such as radiation, surgery, administration of chemotherapeutic agents such as anti-VEGF antibody or combinations thereof.

Most of the FDA approved nanoformulations and other drug delivery systems reported till date are single agent delivery vehicles which pose structural constraints in encapsulation and release of multiple payloads in optimal concentrations at the tumor site. Encapsulation of more than one drug in the same nano-carrier may elicit undesirable drug-drug interaction which might alter the pharmacology of both the drugs, resulting in inefficacy of the drugs. The conventional chemotherapy regimen in an attempt to reduce the tumor volume, do not discriminate between rapidly dividing normal cells and tumor cells, thus leading to severe side-effects.

Therefore, there remains a need for a drug delivery system for delivering combination therapies so that each agent provides the desired maximal effect. Moreover, the drug delivery system must deliver multiple therapeutic agents and independently release these therapeutic agents to the targeted diseased sites.

SUMMARY OF THE INVENTION

A core-shell particle formulation for delivering multiple therapeutic agents is disclosed. The formulation comprises one or more proteins forming a core; and one or more proteins forming a shell encapsulating the core to form a particle formulation. The core and the shell each comprise one or more therapeutic agents, and the particle is configured to independently release therapeutic agents from the core and the shell. In some embodiments the the size of the core-shell particle is 1-1000 nm.

The proteins in the formulation are chosen from the group consisting of human serum albumin, bovine serum albumin, protamine, transferrin, lactoferrin, fibrinogen, gelatin, mucin, soy protein, apoferritin, ferritin, lectin, gluten, whey protein, prolamines, gliadin, hordein, secalin, zein, avenin, and combinations thereof. In some embodiments of the formulation, the core and shell are loaded with different therapeutic agents from the group consisting of cytotoxic drugs, small molecule kinase inhibitors, phytochemicals, deoxyribozymes, ribozymes, siRNA, shRNA, DNA, PNAs, miRNAs, and combinations thereof.

In some embodiments of the formulation the therapeutic agents are chosen from the group consisting of demethylation agents, retinoids, antimetabolites, antimicrotubule agents, anti-angiogenesis agents, alkylating agents, biologic response modifiers, antitumor antibiotics, proteasome inhibitors, topoisomerase I inhibitors, hormones, immunomodulators, monoclonal antibodies, aromatase inhibitors, glucocorticosteroids, cytokines, enzymes, anti-androgen molecules, epigenetic modifiers, imatinib, sorafenib, nilotinib, erlotinib, gefitinib, dasatinib, everolimus, and combinations thereof. In some embodiments the core or the shell or both are embedded with metallic nanoclusters comprising one or more of gold, silver, platinum, copper, or iron.

In some embodiments the therapeutic agents are configured to be delivered by passive targeting from the shell and core either sequentially or simultaneously. In other embodiments the therapeutic agents are configured to be delivered by active targeting from the shell and core either sequentially or simultaneously. The formulation delivered by active targeting is achieved by conjugating the core-shell formulation with monoclonal antibody against CD20, CD33, CD34, CD38, CD44, CD47, CD52 CD90, CD 123, CD 133, EGFR, PDGFR, VEGF, HER2, mTOR, PI3K-Akt, BCR-ABL, SRC, STAT5, MAPK, HER2, transferrin receptors, R.GD, CRGD, LyP-1, bombesin, FSH33, truncated human basic fibroblast growth factor, octreotide, folic acid, mannose, hyaluronic acid, transferrin, somatostatin, or aptamers.

A method of treating a disease, condition or disorder is disclosed, comprising administering to a human patient a therapeutically effective amount of a core-shell particle formulation comprising one or more proteins forming a core and one or more proteins forming a shell encapsulating the core to form a particle formulation; wherein the core and the shell each comprise one or more therapeutic agents, and wherein the particle is configured to independently release therapeutic agents from the core and the shell. The core-shell particle formulation may be administered by local injection, intravenous, subcutaneous, intramuscular or oral delivery.

The method may employ either passively targeting a targeted tissue with the therapeutic agents, or the targeting may be active, and the agents may be delivered from the shell and core either sequentially or simultaneously. The treatment may comprise anticancer therapy, anti-inflammatory therapy, or immunotherapy.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 3A shows computational modeling of albumin-dasatinib and protamine-rapamycin interactions, FIG. 3B shows computationally designed structure of (protamine-rapamycin) (albumin-dasatinib) core-shell nanoparticles.

FIGS. 8A-C show the destabilization of cytoskeleton and distortion of cellular morphology by (protamine-rapamycin) and (albumin-dasatinib) core-shell system as depicted by actin staining.

FIGS. 13A-D illustrate the size distribution and morphological characterization of (protamine-siRNA)-(transferrin-soraf) core-shell nanoparticles using OLS AFM (FIGS. 13A and 13B) and SEM (FIGS. 13C and 13D) showing PS-siRNA nanocore of ~20 nm and (protamine-siRNA)-(transferrin-soraf) core-shell nanoparticles of size ~200 nm.

FIGS. 15A-F demonstrate genomic level effect of the core-shell nanoparticles, FIG. 15A shows dose dependent cytotoxicity in K562 CML cells by protamine-siRNA nanocore, FIG. 15B shows silencing of BCR-ABL oncogene, confirmed by immunoblot (FIG. 15C). FIG. 15D-F show cytotoxicity of transferrin-sorafenib nanoshell through inhibition of phosphor-STAT5.

DETAILED DESCRIPTION OF THE PREFERRED EMBODIMENTS

Figure 1:
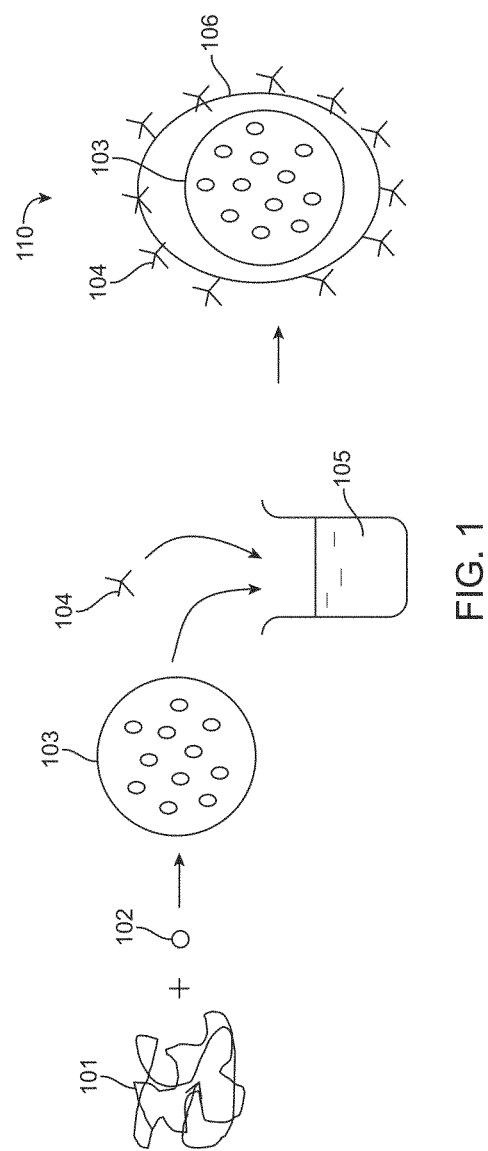
FIG. 1 illustrates a nanoparticle core-shell formulation according to one embodiment.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The term "nanomedicine" as used herein may refer to nanoparticles of two or more proteins, measuring size about 1-1000 nm capable of delivering multiple anti-cancer agents such as chemotherapeutic drugs, small molecule inhibitors etc., in different combinations of at least one small molecule kinase inhibitor and one chemotherapeutic drug or suitable combination of two small molecule inhibitors/chemotherapeutic drugs together. In one embodiment the nanoparticles have a size around 1-500 nm. In another embodiment the nanoparticles have a size around 1-200 nm in size.

"Protein-protein core-shell nanomedicine" may refer to nanomedicine constructs comprising a nano-core formed by one type of protein loaded with one type of chemotherapeutic drug and an outer nano-shell formed by another type of protein loaded with another drug.

Therapeutics may be refer to synthetic drugs including cytotoxic drugs and small molecule kinase inhibitors, phytochemicals or nucleic acid drugs such as siRNAs, shRNAs, miRNAs, PNAs, DNA, DNAzymes, ribozymes, or prodrugs thereof, that have a therapeutic effect against diseases including cancer, inflammatory and auto-immune diseases and the like.

The proposed invention relating to core-shell particle formulation for delivering multiple therapeutic agents is described in the following sections referring to the sequentially numbered figures. The above-mentioned objectives are achieved through the core-shell particle bearing therapeutic agents specifically targeted to the preferred site of action and configured to controllably release therapeutic agents.

Figure 2:
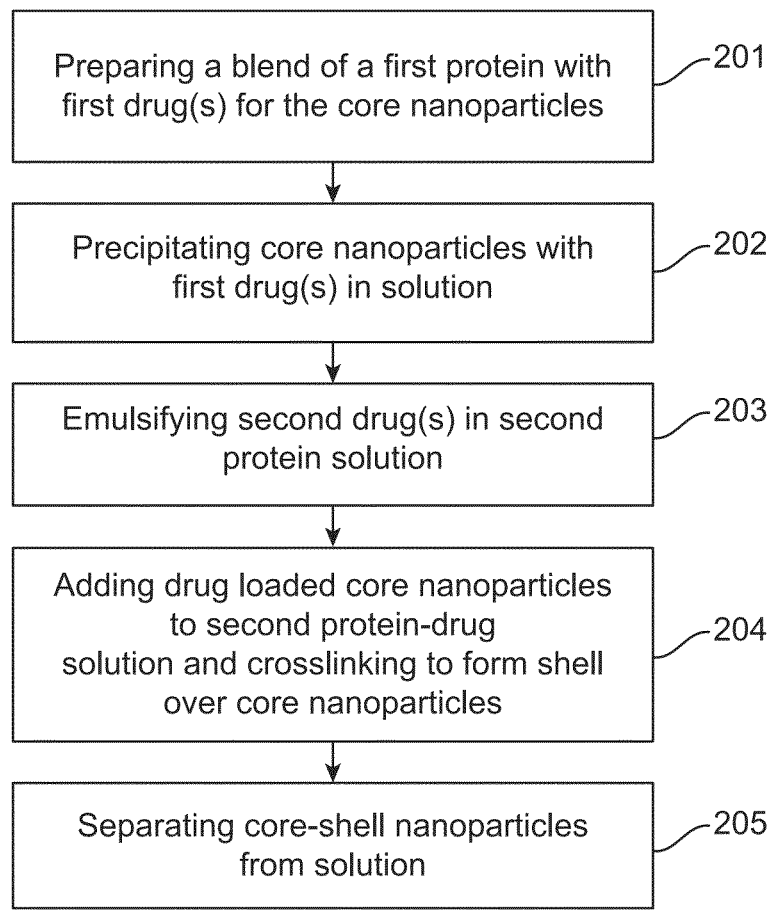
FIG. 2 is a schematic of the method of preparing a core-shell formulation of the invention according to one embodiment.

In one embodiment, core-shell particles for delivering multiple therapeutic agents and methods for their preparation are disclosed, as shown in FIGS. 1 and 2, respectively. As shown in FIG. 1, in one embodiment, the particles of the invention comprise one or more proteins to form a core 101 and one or more proteins forming a shell 106. In various embodiments, the core 101 and the shell 106 each comprise one or more therapeutic agents. In one embodiment of the invention illustrated in FIG. 2, the particle is obtained using the steps shown in the figure. In step 201, a protein precursor solution of the core 101 is reacted with the first therapeutic agent 102 and precipitated to form the drug-loaded core nanoparticles 103 in step 202. In step 203, a second therapeutic agent 104 is blended with a second protein solution 105 for forming the protein shell. The drug-loaded core nanoparticles 103 are added to the blended second protein solution 105 in step 204, in which the therapeutic agent 104 is incorporated into the protein 105 and crosslinked to form a shell 106 around the core 103. Finally, in step 205, the fully formed core-shell nanoparticles 110 with the first therapeutic agent 102 loaded in the core and the second therapeutic agent 104 loaded in the shell are separated from solution for therapeutic use.

In various embodiments, the protein 105 forming the core 101 and shell 106 is chosen from human serum albumin, bovine serum albumin, protamine, transferrin, lactoferrin, fibrinogen, gelatin, mucin, soy protein, apoferritin, ferritin, lectin, gluten, whey protein, prolamines such as gliadin, hordein, secalin, zein, avenin, or combinations thereof.

In various embodiments the protein nanoparticle or the protein shell is formed by a method that is one of nano-precipitation, coacervation, self-assembly, cross-linking, spray drying, electrospray, emulsion desolvation, snap injection, etc. In some embodiments, one or both of the proteins in the core-shell nanoparticle 110 are doped/loaded/embedded with metallic nanoclusters comprising one or more of gold, silver, platinum, copper, or iron for the purpose of tracking the nanoparticles in vivo using one or more of optical, magnetic or x-ray contrast. In some embodiments, the prepared core-shell nanoparticle 110 is purified by centrifugation and lyophilisation.

In one embodiment, the total size of the core-shell particle is of 1-1000 nm. In various embodiments, the core and shell are loaded with one or more small molecule kinase inhibitors or chemotherapeutic drugs. In various embodiments, the shell comprises either hydrophilic or hydrophobic therapeutic agents, or both types of agents.

In one embodiment, the core and shell are loaded with different therapeutic agents comprising synthetic chemotherapeutic drugs including cytotoxic drugs or one or more small molecule kinase inhibitors or phytochemicals or nucleic acid drugs such as deoxyribozymes, ribozymes, siRNA, shRNA, DNA, PNAs, or miRNAs or combinations thereof.

In various embodiments, the chemotherapeutic drug is chosen from one or more of demethylation agents, retinoids, antimetabolites, antimicrotubule agents, anti-angiogenesis agents, alkylating agents, biological response modifiers, antitumor antibiotics, proteasome inhibitors, topoisomerase I inhibitors, hormones, immunomodulators, monoclonal antibodies, aromatase inhibitors, glucocorticosteroids, cytokines, enzymes, anti-androgen molecules, epigenetic modifiers, or small molecule kinase inhibitors including imatinib, sorafenib, nilotinib, erlotinib, gefitinib, dasatinib, everolimus.

In various embodiments, the nanoparticles comprising the therapeutic agents 102 and 104 are configured to be delivered as formulations with excipients suitable for local injection, or intravenous, subcutaneous, intramuscular or oral delivery. In some embodiments the formulations are configured to deliver therapeutic agents to targeted tissue by either passive or active targeting. In one embodiment, the active targeting is done by conjugating the core-shell formulation with targeting ligands such as monoclonal antibody against receptors such as, CD20, CD33, CD34, CD38, CD44, CD47, CD52 CD90, CD 123, CD 133, EGFR, PDGFR, VEGF, HER2, mTOR, PI3K-Akt, BCR-ABL, SRC, STAT5, MAPK, HER2, transferrin receptors and like, peptides such as R.GD, CRGD, LyP-1, bombesin (BBN), FSH33, truncated human basic fibroblast growth factor (tbFGF), octreotide, folic acid, mannose, hyaluronic acid (HA), proteins such as transferrin, somatostatin or aptamers. In one embodiment, the therapeutic agents are configured to be delivered to tissue from the shell and core either sequentially or simultaneously.

In various embodiments, a method of treatment of treatment against cancer, inflammatory or auto-immune diseases is disclosed, comprising delivering to targeted tissue, a therapeutically effective amount of a formulation comprising the core-shell nanoparticles as illustrated in various earlier embodiments. The method in various embodiments may involve administering the formulation to a human patient by local injection, intravenous, subcutaneous, intramuscular or oral delivery. The method in some embodiments may target the therapeutic agents to specific tissue.

The method in some embodiments may involve either simultaneous release of the therapeutic agents from the core of the nanoparticles, and in other embodiments the agents may be released sequentially, as required. In some embodiments, the method may use passive targeting of tissue, while in other embodiments the therapeutic agents are delivered by active targeting. In some embodiments of the method the nanoparticles are tracked in vivo using one or more of optical, magnetic or x-ray contrast.

The particle formulations disclosed in the various embodiments above are configured to independently release first therapeutic agents 102 from the core 101 and second therapeutic agents 104 from the shell 106. This gives the nanocarrier an extraordinary ability to deliver multiple therapeutic molecules directly to specific cells rather than systemically to all cells and, further, to deliver both the drugs into the cell, thereby potentially reducing dosages at equivalent efficacy. Further the use of two separate protein phases is envisioned, rather than synthetic materials as in engineered nanoparticles. Use of proteins as a nanocarrier is considered because of the reduced toxicity of such natural materials. A second part of this invention is the modification of one or more of the proteins by doping/embedding them with metallic nanoclusters of gold or other suitable metals nanoclusters for imparting specific characteristic properties to the nanocarrier such as optical/magnetic/x-ray contrast. This enables tracking of the nanoparticles in-vivo and understanding their bio-distribution and location.

One application wherein such a drug delivery system can be especially useful is in cancer or tumor formation. Tumorigenesis is a multi-step process, where the genetic alterations enable the cancer cells to acquire properties such as self-sufficiency of growth signals, insensitivity to anti-growth signals evasion of apoptosis, limitless replicative potential, sustained angiogenesis which further lead to tissue invasion and metastasis. Unlike the cytotoxic chemotherapeutic drugs, protein kinase inhibitors target specifically the protein kinases, which are deregulated (constitutively activated/mutated/over-expressed) in cancer cells. Moreover, most of the kinase inhibitors have been found to have low levels of undesirable side effects in clinical and preclinical studies compared to cytotoxic drugs. Yet, for highly aggressive and metastatic cancers, cytotoxic drugs present an immediate effect compared to kinase inhibitors. Resistance to kinase inhibitors in the long run due to point mutations in the drug-binding domain of kinases eventually distorts the conformation of drug binding domain and hence prevents the drug from binding to it. In certain cases, kinase inhibition of the primary oncoprotein can lead to the activation or over-expression of a secondary survival signal in the oncogenic network. In those cases monotherapy with a single therapeutic agent remains ineffective. Combination of cytotoxic chemotherapeutic drugs and kinase inhibitors can be an attractive approach to treat highly aggressive tumor masses. The current invention enables combination therapy using bio-friendly protein based nanocarriers, and attempts to solve most of the issues associated with conventional treatment strategy.

The invention is further illustrated with reference to the following examples, which however, are not to be construed to limit the scope of the invention as defined by the appended claims.

EXAMPLES

Example-1

Synthesis of (Protamine-Rapamycin) Nanocore:

Synthesis of protamine-rapamycin nanocore: protamine-rapamycin nanocore was prepared using aqueous chemical route. The cationic peptide protamine (10 kDa) was dissolved at a concentration of 11 mg/ml in nuclease and endotoxin free water. Rapamycin was dissolved in DMSO as per the manufacturer's instructions. Rapamycin was added to aqueous solution of protamine. The complexation of protamine and rapamycin resulted in a turbid solution, which was vortexed vigorously and incubated at room temperature for 30 min to enable the effective complexation of rapamycin with protamine. Thus formed protamine-rapamycin nanocore was purified by dialysis using 2 kDa cut off dialysis membrane.

Synthesis of (Protamine-Rapamycin)-(Albumin-Dasatinib) Core-Shell Nanomedicine:

Dasatinib in DMSO was mixed with aqueous solution of albumin at a dasatinib final concentration of 100 μM. In a typical synthesis, 100 μM dasatinib in albumin was added drop-wise to protamine-rapamycin solution. The solution was kept under continuous stirring for ~30 m at room temperature. The individual HSA molecules were cross-linked using 2 mg 1-Hhyl-3-[3dimethylaminopropyl]carbodiimide hydrochloride (EDC), a zero-length cross-linker for effective entrapment of the therapeutic molecules m the protein shell. The reaction was continued for ~2 h at room temperature. The solution was further subjected to dialysis using dialysis cassettes with 2 kDa molecular weight cut off and lyophilized for 48 h. The percentage entrapment of the drug was determined from standard graph of rapamycin and dasatinib.

Example-2

Figure 3B:
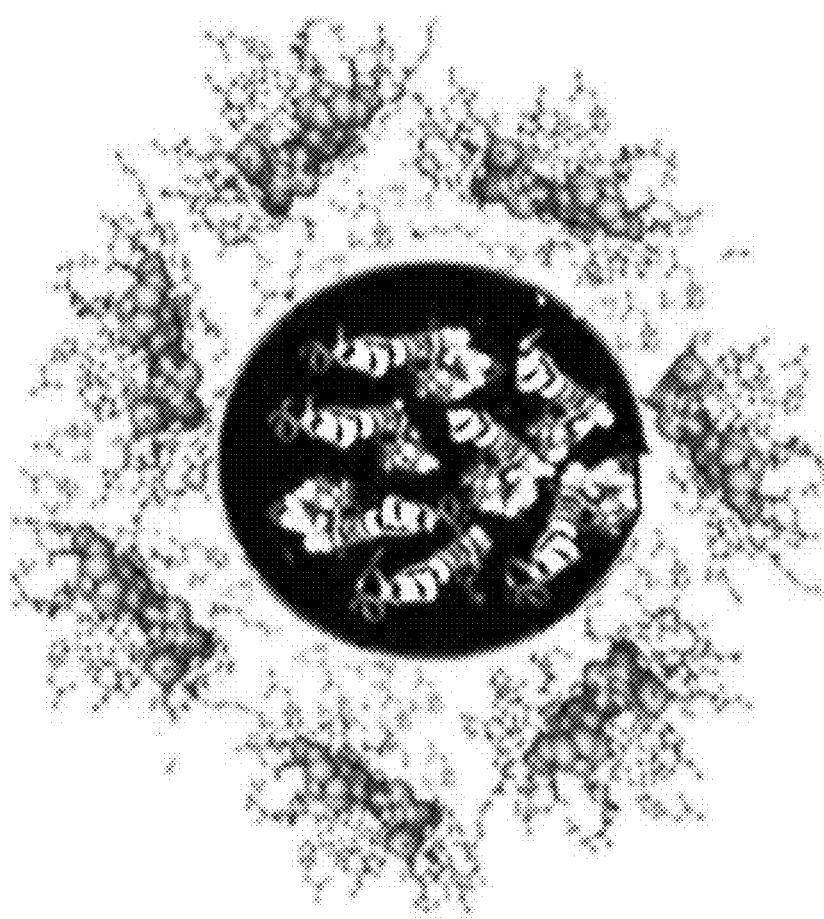
FIGS. 3A and 3B show an example with two rapamycin and dasatinib docked protamine and albumin respectively, in a core-shell architecture.
Figure 3A:
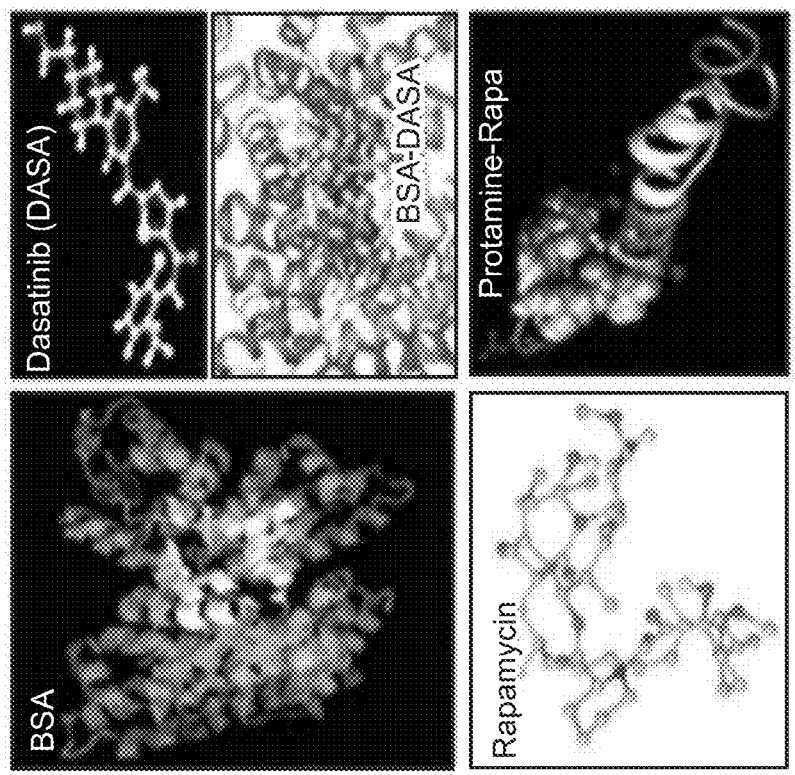

Computational Modeling of (Protamine-Rapamycin)-(Albumin-Dasatinib) Core-Shell Nanomedicine:

The computational modeling of two different drug molecules (rapamycin and dasatinib) docked to two different proteins (protamine and albumin) in a core-shell architecture is designed. Computational modeling of albumin-dasatinib and protamine-rapamycin interactions is shown in FIG. 3A and computationally designed structure of (protamine-rapamycin) (albumin-dasatinib) core-shell nanoparticles is shown in FIG. 3B.

Figure 4B:
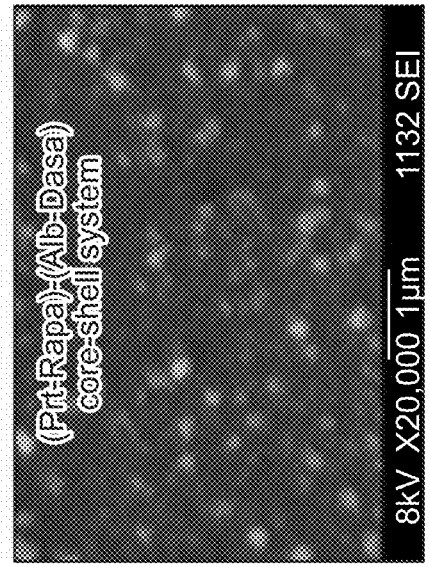
FIGS. 4A-C illustrate the size distribution of (protamine-rapamycin) and (albumin-dasatinib) core-shell system.
Figure 4C:
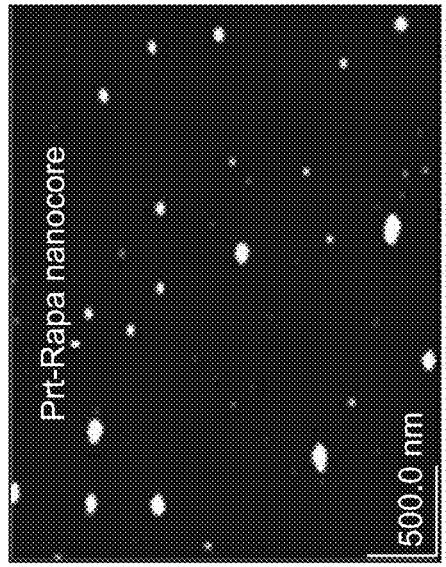
Figure 4A:
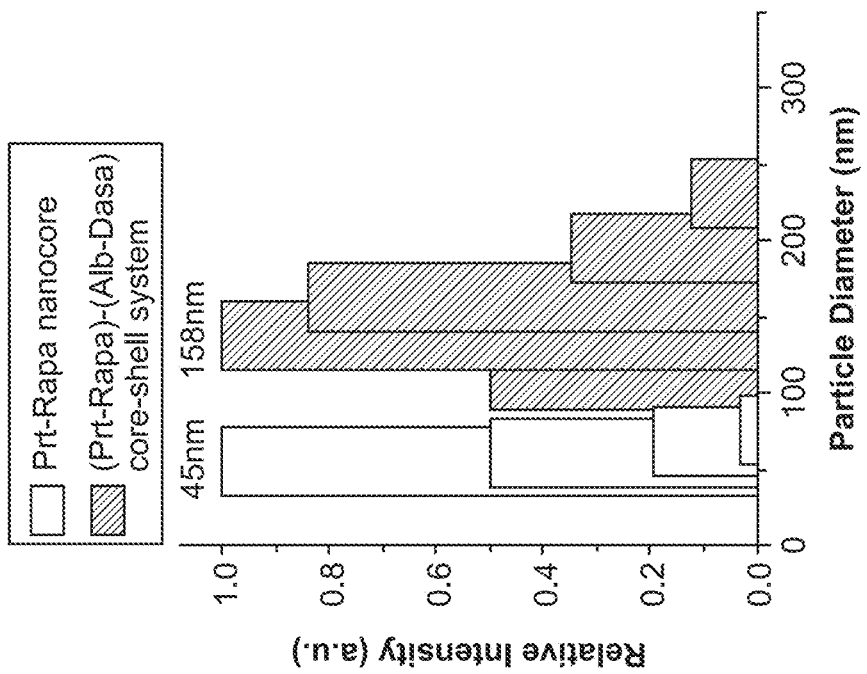
Figure 5A:
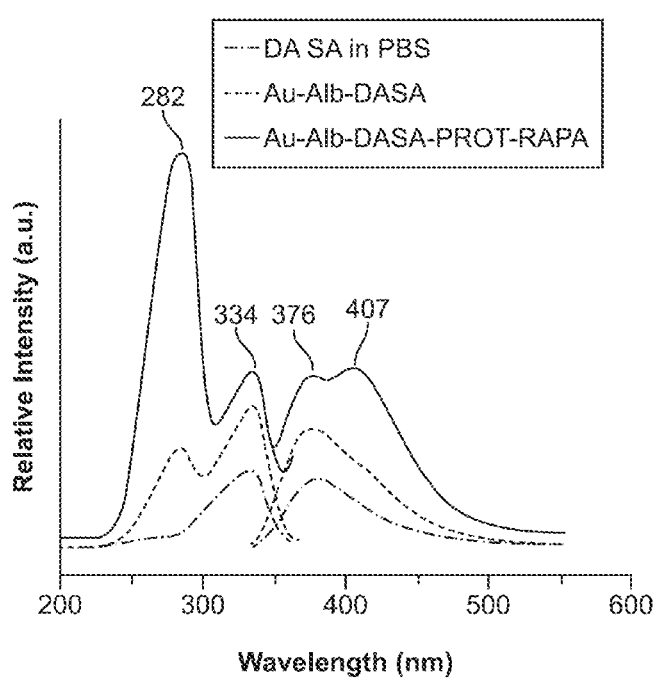
FIG. 5A and FIG. 5B show the photoluminescence spectra of (protamine-rapamycin) and (albumin-dasatinib) core-shell system, where albumin is doped with metallic nanoclusters of gold.
Figure 5B:
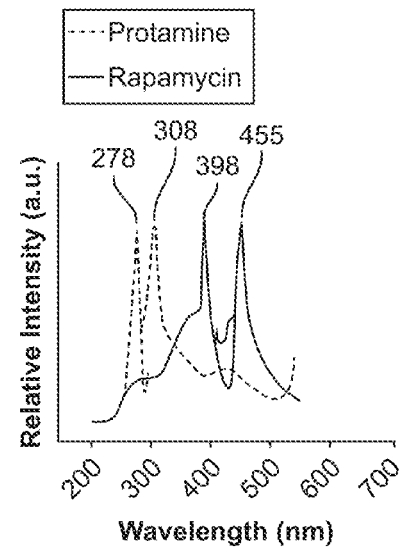
Figure 6A:
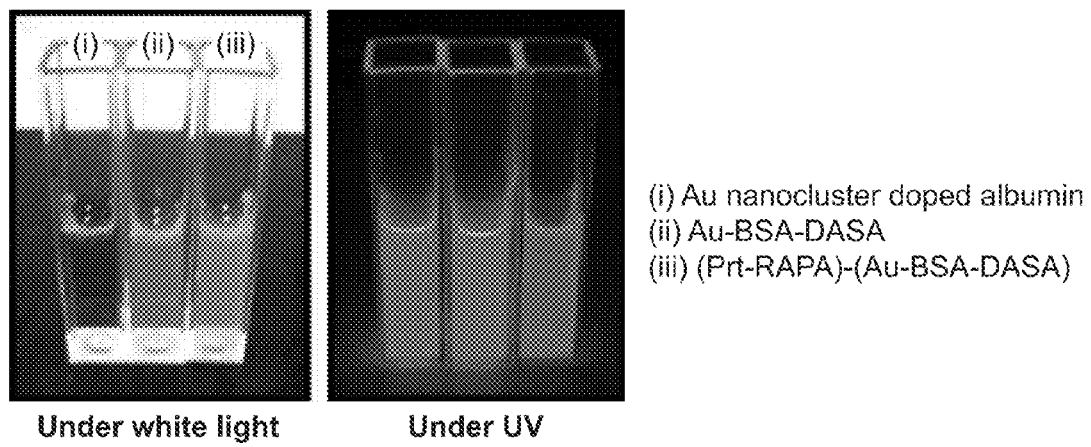
FIG. 6A show the red-NIR emission from gold nanocluster doped protein-protein core-shell nanomedicine and FIG. 6B show the corresponding photoluminescence excitation-emission spectrum.
Figure 6B:
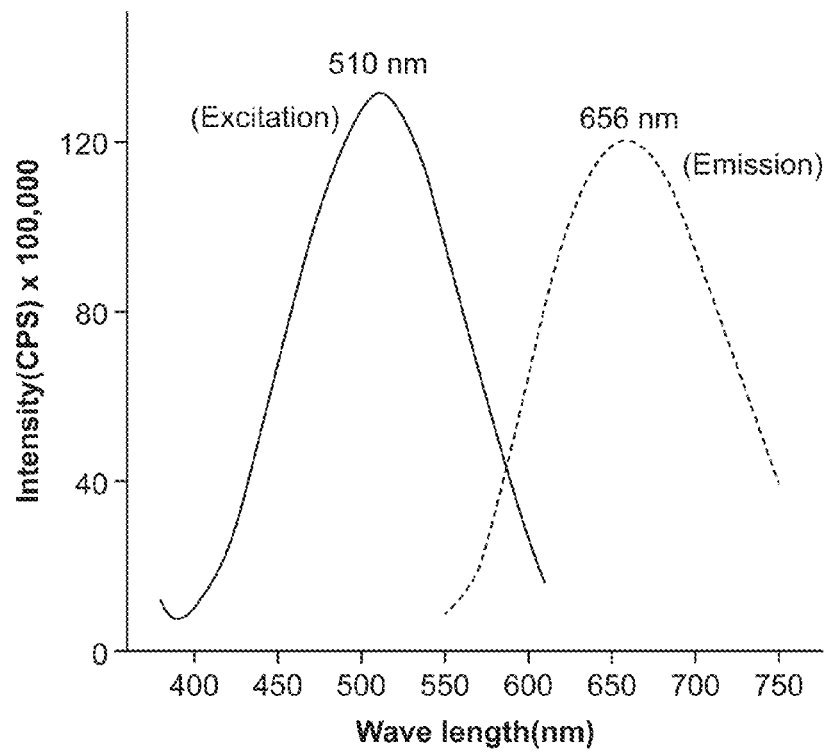

Characteristics of (Protamine-Rapamycin)-(Albumin-Dasatinib) Core-Shell Nanomedicine:

FIG. 4 shows an example of the result with the size distribution of (protamine-rapamycin) and (albumin-dasatinib) (FIG. 4A) core-shell system using dynamic light scattering (DLS) showing a core of size around 45 nm and a core-shell structure of size around 158 nm (FIG. 4B) atomic force microscopy (AFM) and (FIG. 4C) scanning electron microscopy showing the spherical morphology of the particles formed. The photoluminescence spectra of (protamine-rapamycin) and (albumin-dasatinib) core-shell system, where albumin is doped with metallic nanoclusters of gold is shown in FIGS. 5A and 5B. Further, the red-NIR emission from gold nanocluster doped protein-protein core-shell nanomedicine and the corresponding photoluminescence excitation-emission spectrum is shown in FIGS. 6A and 6B.

Example-3

Figure 7:
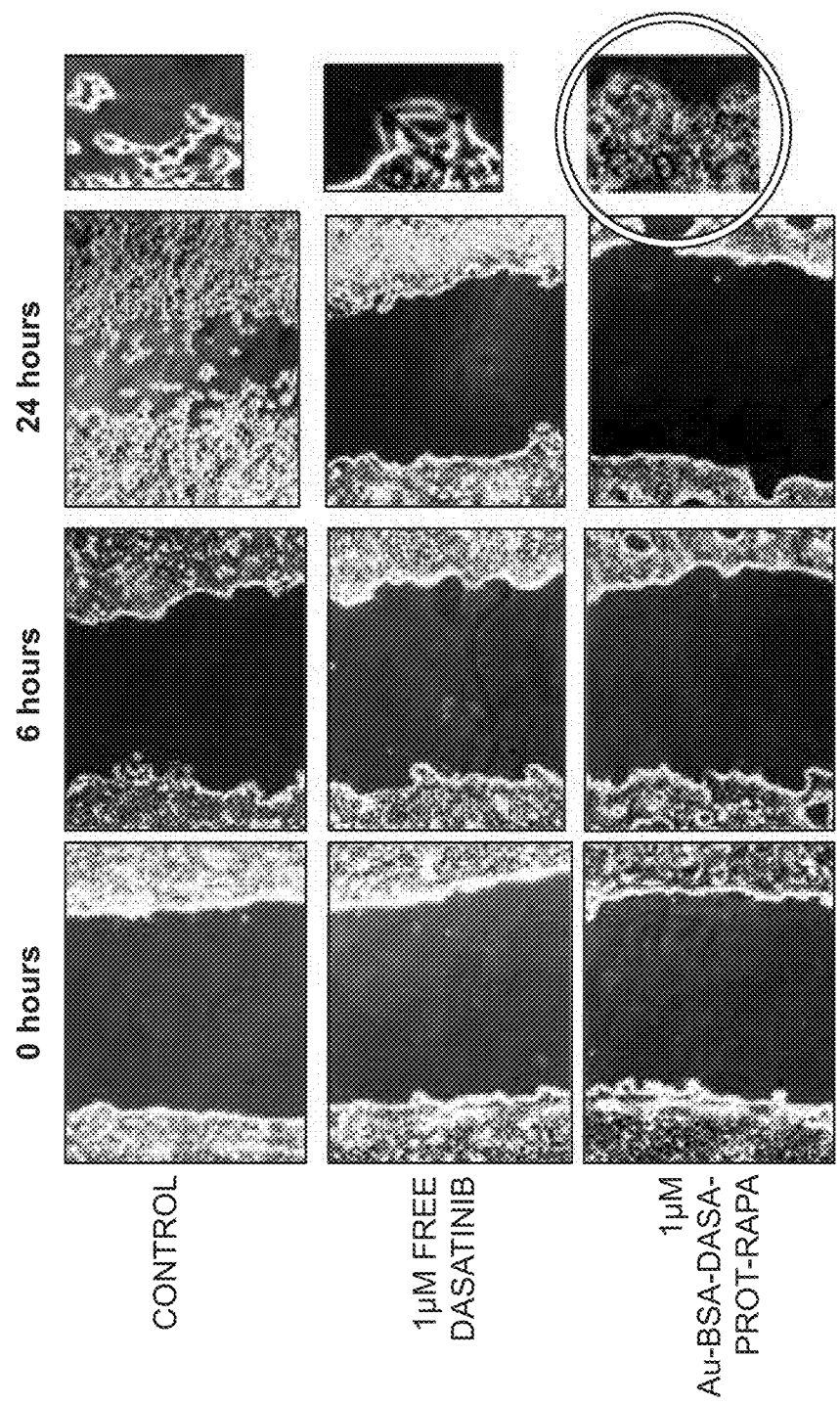
FIG. 7 is illustrates the improved efficacy of the (prt-rapa)-(alb-dasa) core-shell nanomedicine in cancer cell migratory potential. The encircled image shows the distorted morphology of breast adenocarcinoma cells treated with the protein-protein core-shell nanomedicine comprising of gold nanocluster doped (prt-rapa)-(alb-dasa).

Results of Nanomedicine Treatment Against Breast Cancer:

The protamine-rapamycin) and (albumin-dasatinib) core-shell nanomedicine is administered either intravenously, orally, parenterally, subcutaneously or by direct local delivery. The method of treatment of cancer-like diseases using core-shell nanomedicine aiding combinatorial anti-cancer therapy by sequential or simultaneous delivery of a combination of small molecule kinase inhibitor and chemodrugs. of the (prt-rapa)-(alb-dasa) core-shell nanomedicine in cancer cell migratory potential shows an improved efficacy in FIG. 7. The encircled image shows the distorted morphology of breast adenocarcinoma cells treated with the protein-protein core-shell nanomedicine comprising of gold nanocluster doped (prt-rapa)-(alb-dasa). FIG. 8 shows the destabilization of cytoskeleton and distortion of cellular morphology by (protamine-rapamycin) and (albumin-dasatinib) core-shell system as depicted by actin staining.

Figure 9A:
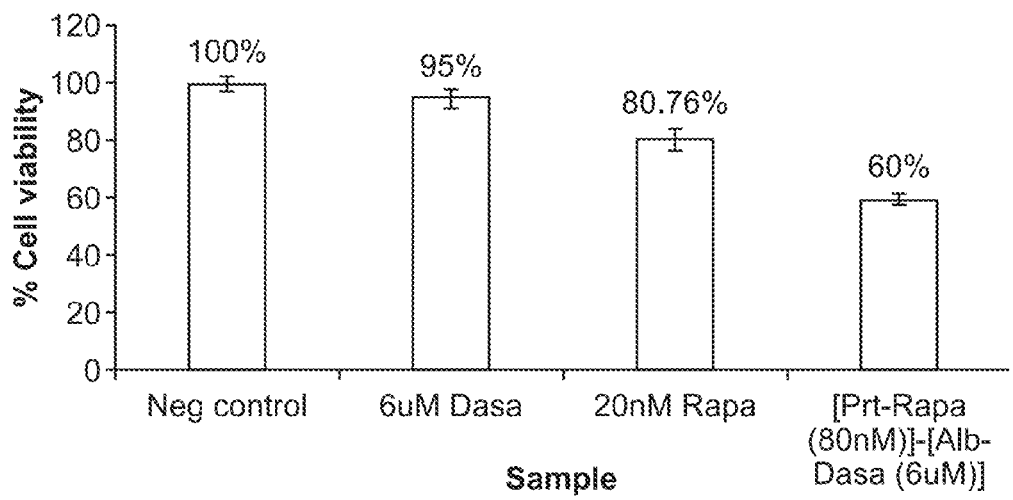
FIGS. 9A-C show the quantitative data with substantially improved cytotoxicity of (prt-rapa)-(tf-dasa) core-shell system in highly aggressive breast carcinoma cells with increasing concentrations of rapamycin and constant dasatinib concentration.
Figure 9B:
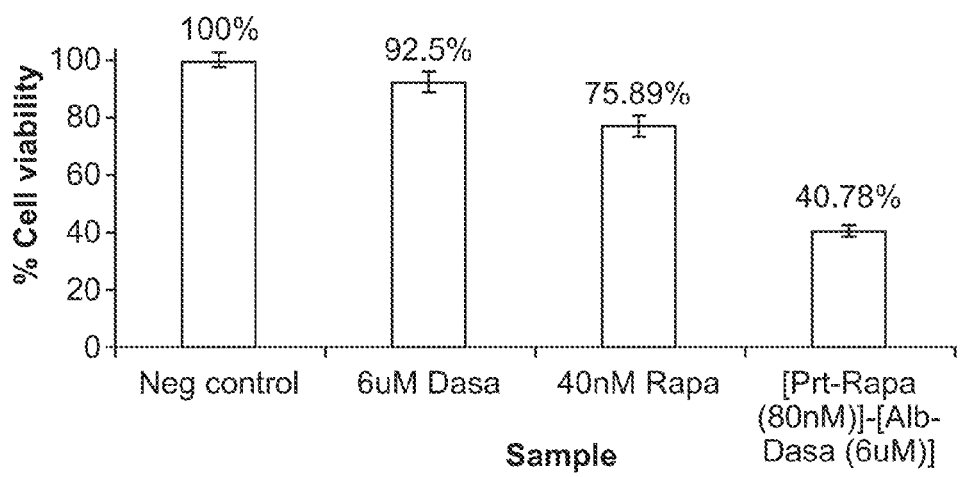
Figure 9C:
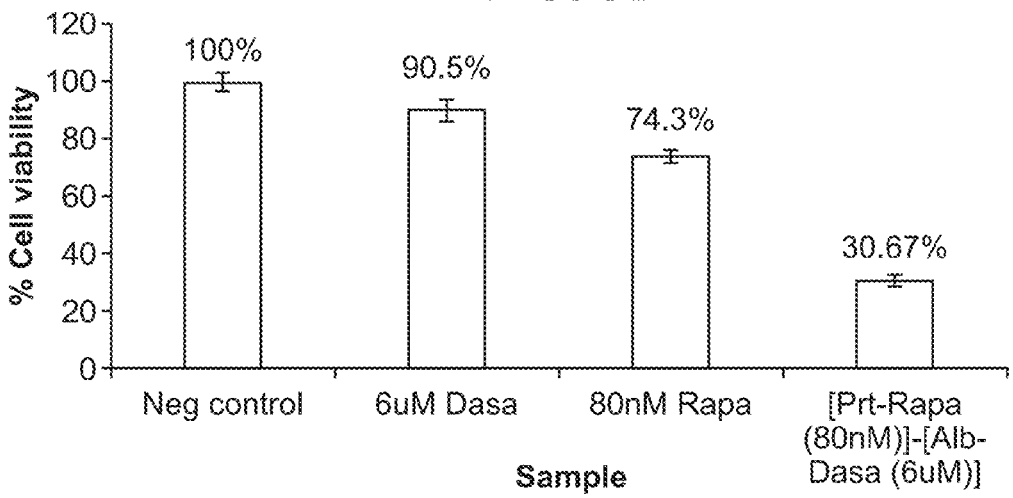

Further in another combination, the treatment shows the quantitative data with substantially improved cytotoxicity of (protamine-rapamycin) and (transferrin-dasatinib) core-shell system is shown in FIG. 9. The improved toxicity against highly aggressive breast carcinoma cells with increasing concentrations of rapamycin and constant dasatinib concentration is proved in FIGS. 9A, 9B and 9C.

Example-4

Synthesis of Protamine Imatinib-Albumin Sorafenib Nanomedicine Against Drug Resistant Chronic Myeloid Leukemia (CML)—Synthesis of Protamine-Imatinib Nanocore:

Protamine-rapamycin nanocore was prepared using aqueous wet chemical route. The cationic peptide protamine (10 kDa) was dissolved at a concentration of 1 mg/ml in nuclease and endotoxin free water. Imatinib was dissolved m DMSO, as per the manufacturer's instructions imatinib was added to aqueous solution of protamine. The solution was vortexed vigorously and incubated at room temperature for 30 m to enable the effective complexation of imatinib with protamine.

Figure 10:
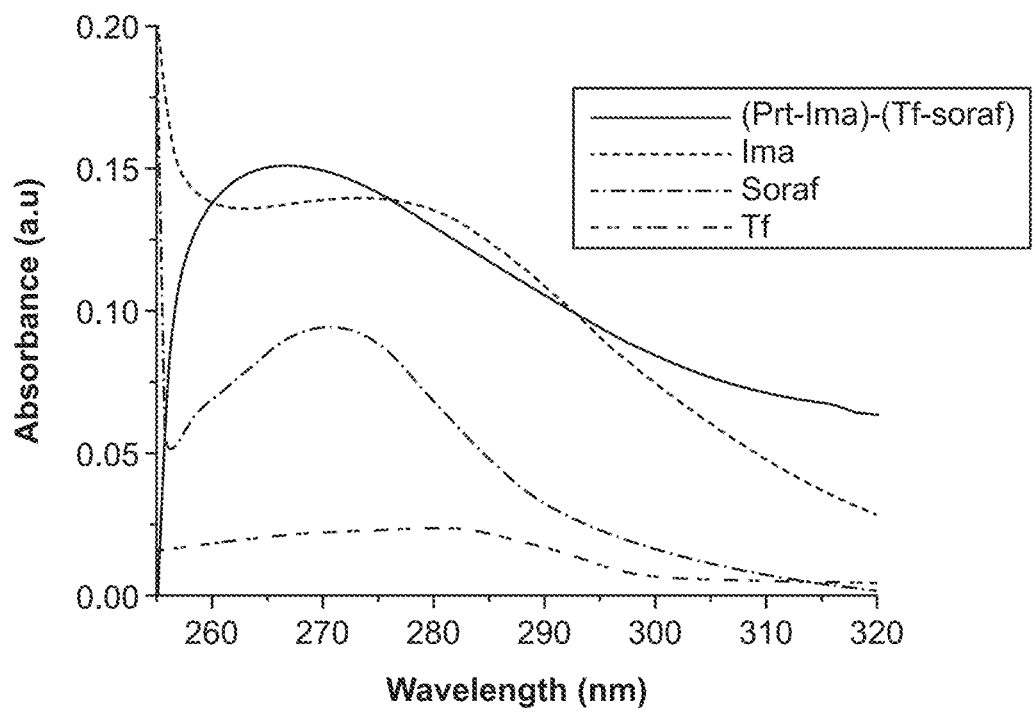
FIG. 10 shows UV-VIS absorption spectra of (protamine-imatinib) and (transferrin-sorafenib) core-shell nanomedicine.
Figure 11:
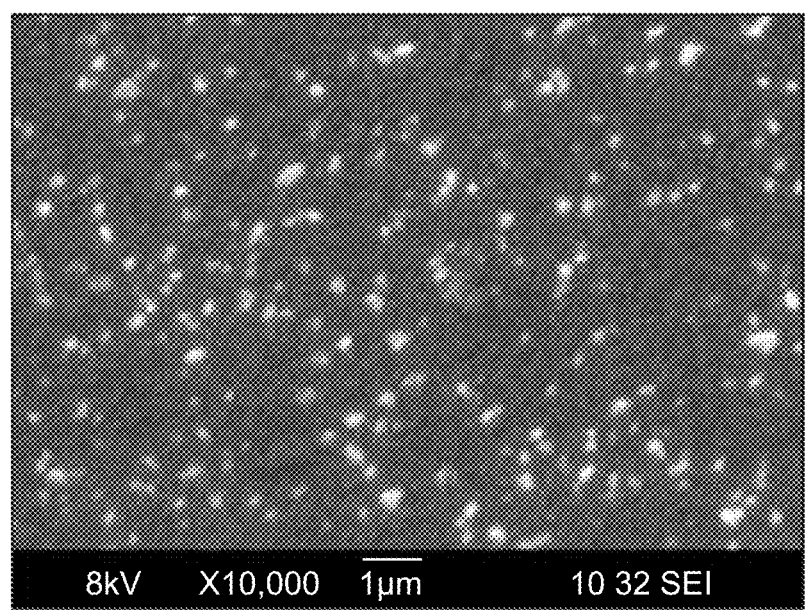
FIG. 11 is a scanning electron microscopic image of (protamine-imatinib) and (transferrin-sorafenib) core-shell nanomedicine showing spherical particles of ~200 nm.

Characteristics of (Protamine-Imatinib)-(Transferrin-Sorafenib) Core-Shell Nanomedicine:

In another combination, the synthesis of (protamine-imatinib) and (transferrin-sorafenib) core-shell nanomedicine is done as steps followed in the above method. The UV-VIS absorption studies are shown in FIG. 10. The scanning electron microscopic image of (protamine-imatinib) and (transferrin-sorafenib) core-shell nanomedicine with spherical particles of ~200 nm is shown in FIG. 11.

Example-5

Figure 12:
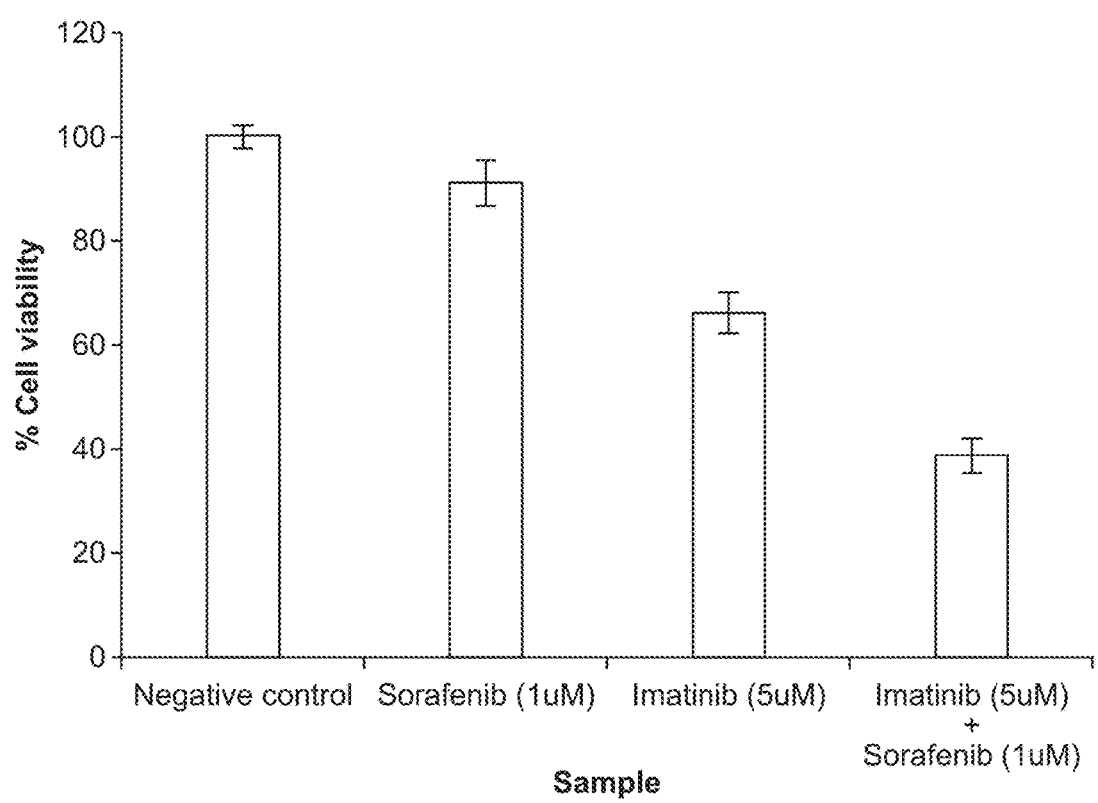
FIG. 12 illustrates the improved cytotoxicity of (protamine-imatinib) and (transferrin-sorafenib) core-shell nanomedicine in drug resistant CML cells carrying amplification of BCR-ABL and STAT5 activation.

Results of (Protamine-Imatinib)-(Transferrin-Sorafenib) Core-Shell Nanomedicine Against Chronic Myeloid Leukemia (CML):

The composition of sorafenib with 1 µM in the protamine shell and imatinib with 5 µM in the transferrin shell shown an improved cytotoxicity against the chronic myeloid leukemia (CML) cells. The improved cytotoxicity of (protamine-imatinib) and (transferrin-sorafenib) core-shell nanomedicine in drug resistant CML cells carrying amplification of BCR-ABL and STAT5 activation is shown in FIG. 12.

Example-6

Synthesis of (Protamine-imatinibH)-(Albumin-Dasatinib) Core-Shell Nanomedicine:

Sorafenib in DMSO was mixed with aqueous solution of albumin at a sorafenib final concentration of 100 µM. In a typical synthesis, 100 µM sorafenib in albumin was added drop-wise to protamine-imatinib solution. The solution was kept under continuous stirring, for 30 m at room temperature. The individual HSA molecules were crosslinked using 2 mg 1-Ethyl-3-[3-dimethylaminopropyl]carbodiimide hydrochloride (EDC), a zero-length cross-linker for effective entrapment of the drug in the protein shell. The reaction was continued for 2 h at room temperature. The solution was further subjected to dialysis using dialysis cassettes with 2 kDa molecular weight cut off and lyophilized for 48 h. The percentage entrapment of the drug was determined from standard graph of imatinib and sorafenib.

Example-7

Synthesis of Protamine siRNA-Albumin Sorafenib Nanomedicine Conjugated to Transferrin—Synthesis of Protamine siRNA Nanoconjugates:

Protamine-siRNA nanoconjugates were prepared using aqueous wet chemical route, with an N/P ratio of 12. The cationic peptide, protamine (10 kDa) was dissolved at a concentration of 11 mg/ml in nuclease and endotoxin free water. Lyophilized powder of siRNA targeted to BCR-ABL fusion kinase transcript in chronic myeloid leukemia (CML) was dissolved in RNase free water as per the manufacturer's instructions to prepare a stock solution of 350 nM. Protamine solution was added drop-wise to siRNA solution at the respective N/P ratio. The complexation of protamine and siRNA resulted in a turbid solution which was vortexed vigorously and incubated at room temperature for 30 min to enable the effective complexation of siRNA with protamine.

Characteristics of (Protamine-siRNA)Transferrin-Sorafenib) Core-Shell Nanomedicine.

The result of the size distribution and morphological characterization of (protamine-siRNA)-(transferrin-sorafenib) core-shell nanoparticles using OLS AFM and SEM showing PS-siRNA nanocore of ~20 nm and (protamine-siRNA)-(transferrin-soraf) core-shell nanoparticles of size ~200 nm is shown in FIG. 13.

Synthesis of Albumin Sorafenib Nanoconjugates:

Albumin-sorafenib nanoparticles were prepared using an aqueous wet chemical route. Sorafenib, which is a multi-kinase inhibitor targeting STAT5 kinase in drug resistant CML was prepared in DMSO and aliquots were stored at −20° C. In a typical synthesis, 15.7 mM sorafenib tosylate in DMSO was added drop-wise to 5 mg/ml HSA solution. The solution was kept under continuous stirring where the final concentration of sorafenib was adjusted to 500 µM. The stirring was continued for 30 m at room temperature. The individual HSA molecules were cross-linked using 2 mg 1-Ethyl-3-[3dimethylaminopropyl]carbodiimide hydrochloride (EOC), a zero-length cross-linker for effective entrapment of the drug in the protein shell. The reaction was continued for ~2 h at room temperature. Sorafenib embedded albumin nanoparticles (nAlb-Soraf) were subjected to dialysis using dialysis cassettes with 2 kDa molecular weight cut off and lyophilized for 48 h. The percentage entrapment of the drug was determined from standard graph of sorafenib prepared in DMSO.

Example-8

Synthesis of Protamine sIRNA-Transferrin Sorafenib Nanomedicine Doped with Metallic Nanoclusters:

The preparation of protamine-siRNA nanoconjugates is done as described in example 3. In this method of preparation, the carrier protein itself possesses cancer cell specific targeting capability. Transferrin used for encapsulating the small molecule kinase inhibitor is pre-doped with metallic nanoclusters of gold, platinum, silver etc. for imparting specific characteristics such as optical contrast, magnetic contrast or and/or cationic zeta potential. The precursors of metals are added to protein solution at 37° C. at 10 mM concentration kept under stirring. The reduction of the metal ions to metallic nanoclusters is aided by reducing agents such as NaOH, ascorbic acid etc. The resulting solution is purified using desalting columns and further used for preparing transferrin-sorafenib nanoconjugates as described in example 3, which is further used for complexation with protamine-siRNA nanoconjugates to form protein-protein composite nanomedicine.

Example-9

Figure 14A:
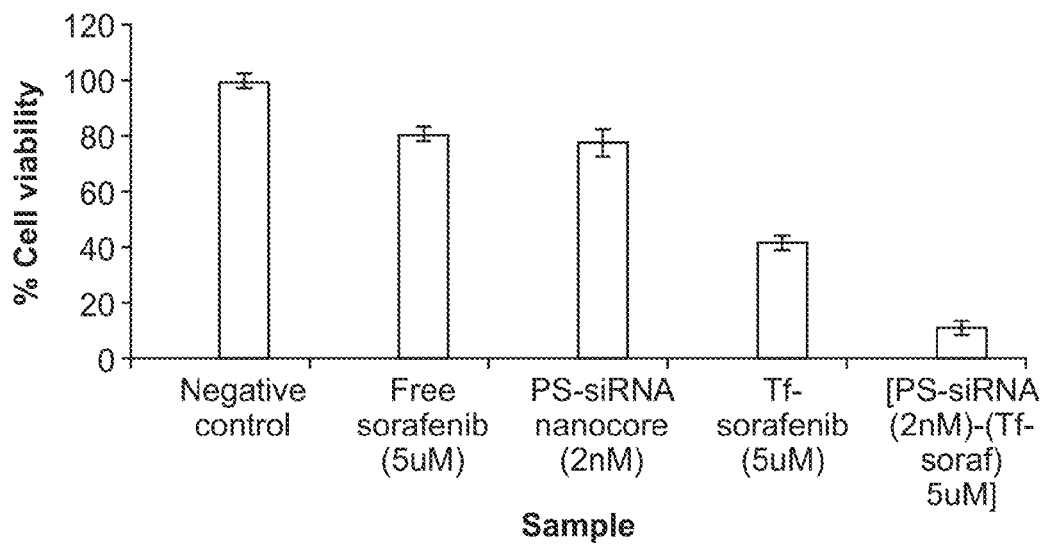
FIG. 14A shows cytotoxic effect of (protamine-siRNA)-(transferrin-soraf) in drug resistant CML cells carrying amplification of BCR-ABL and STAT5 activation and FIG. 14B shows normal healthy cells, which remain 100% viable upon treatment with (protamine-siRNA) and (transferrin-soraf).
Figure 14B:
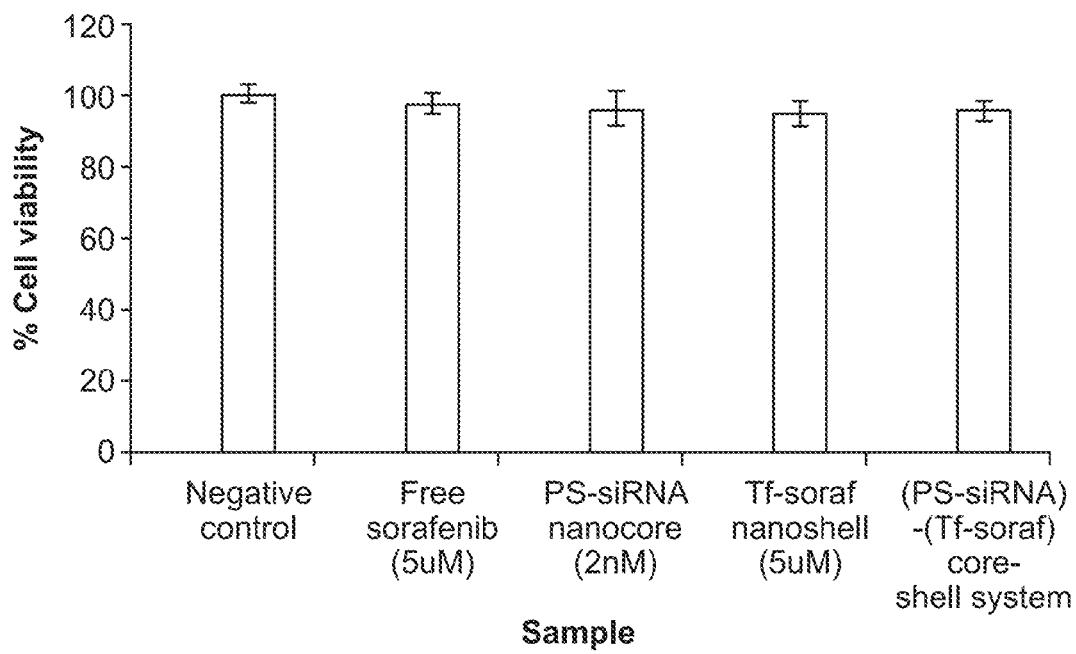
Figures 16A, 16B:
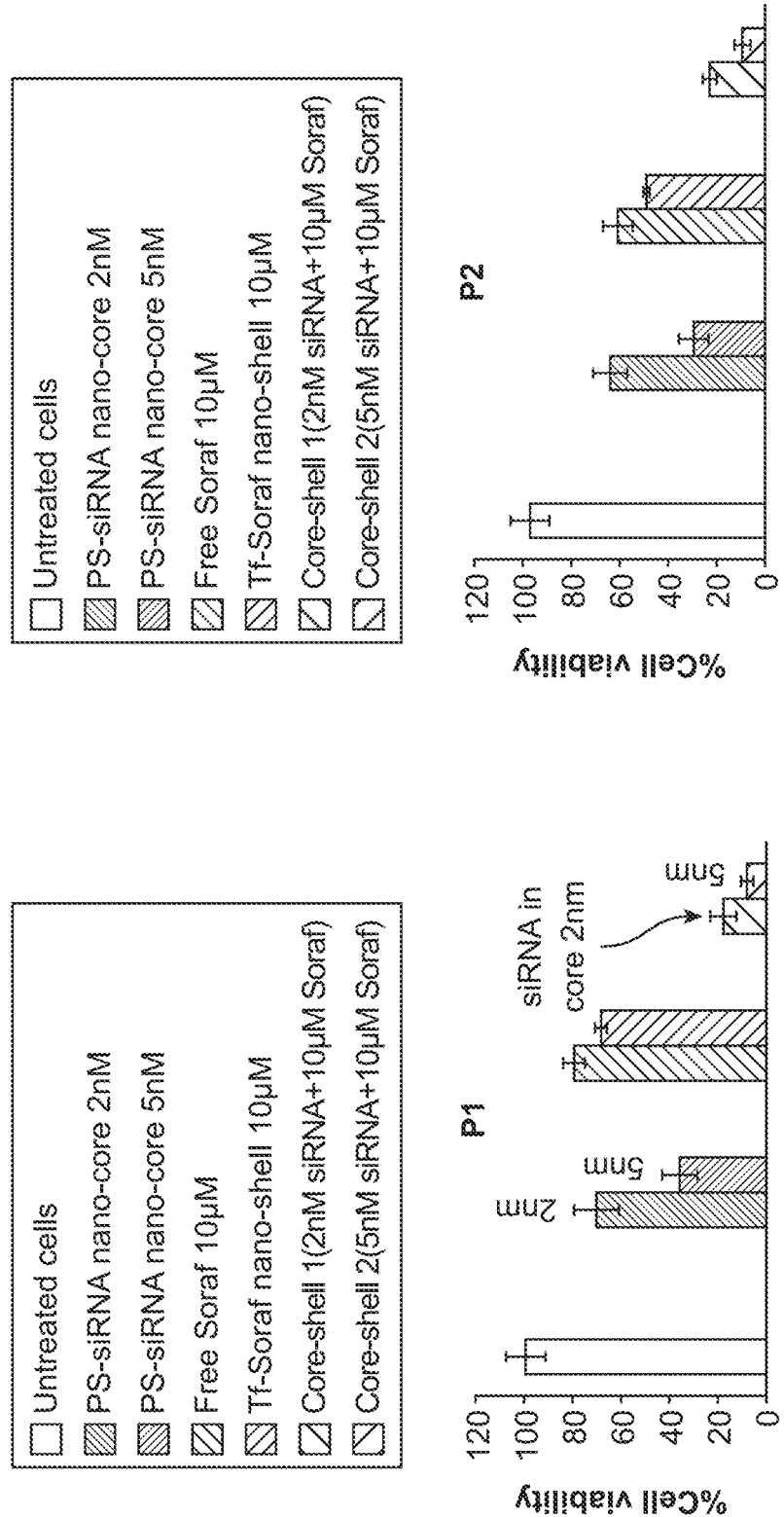
FIGS. 16A-N show cytotoxicity of protamine siRNA-Albumin Sorafenib nanomedicine in vitro, on leukemic cells from 14 patients exhibiting enhanced cytotoxicity against core-shell NPs compared to core alone or shell alone.
Figures 16C, 16D:
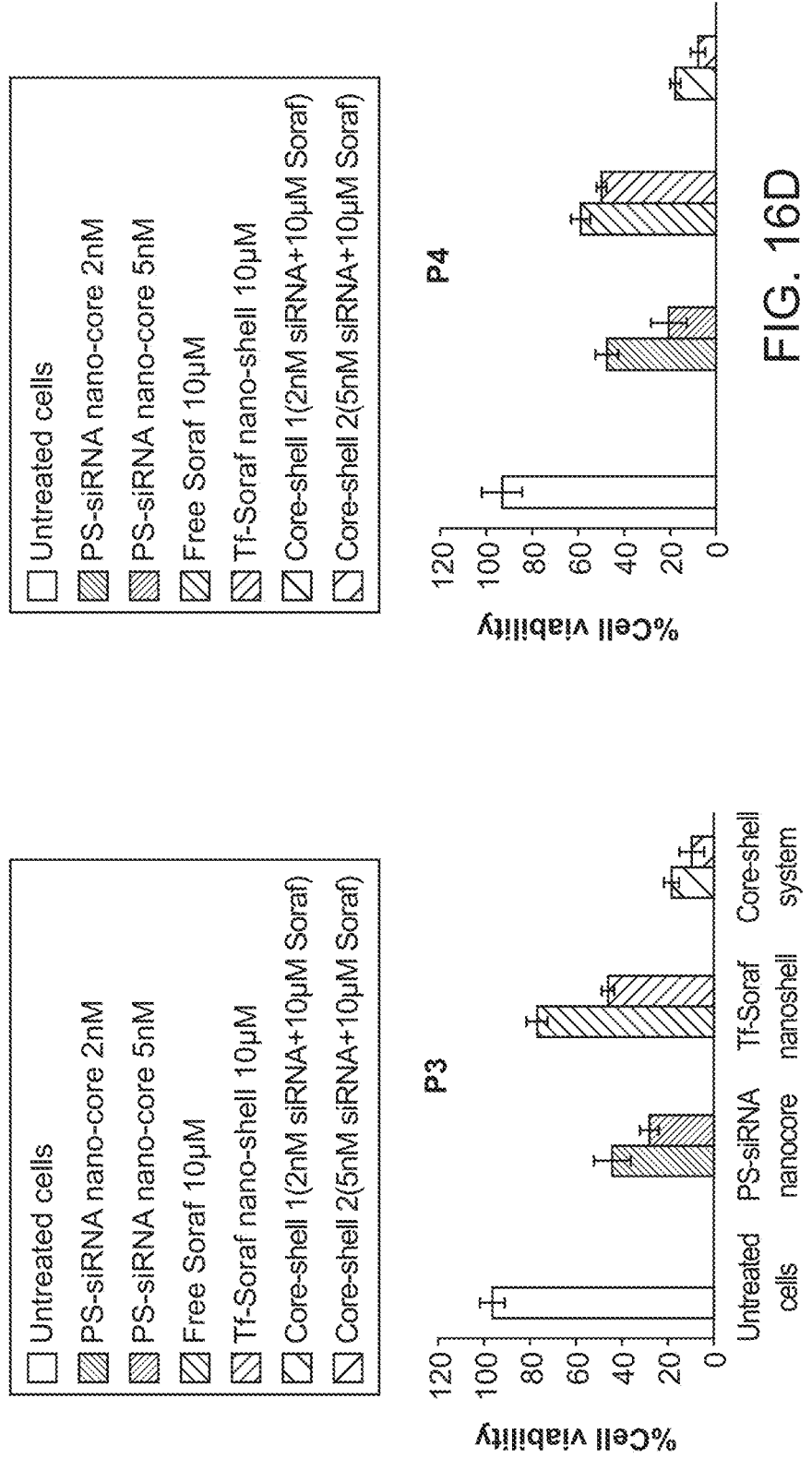
Figure 16G:
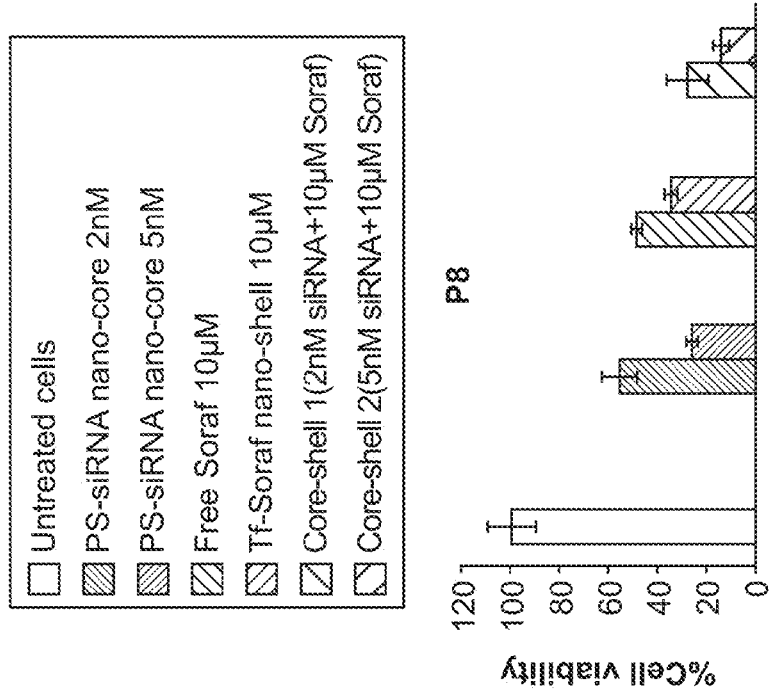
Figure 16H:
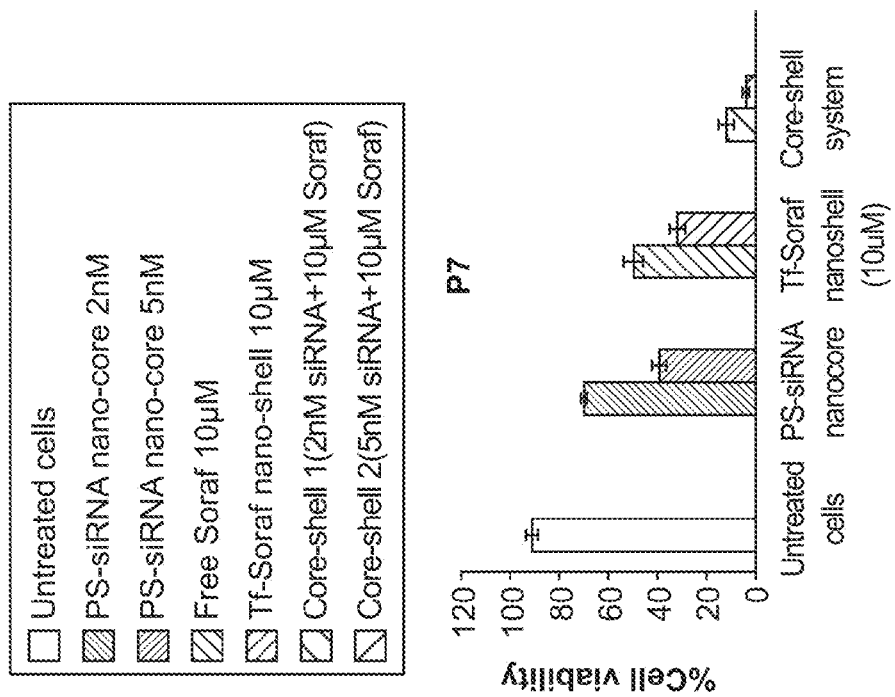
Figures 16I, 16J:
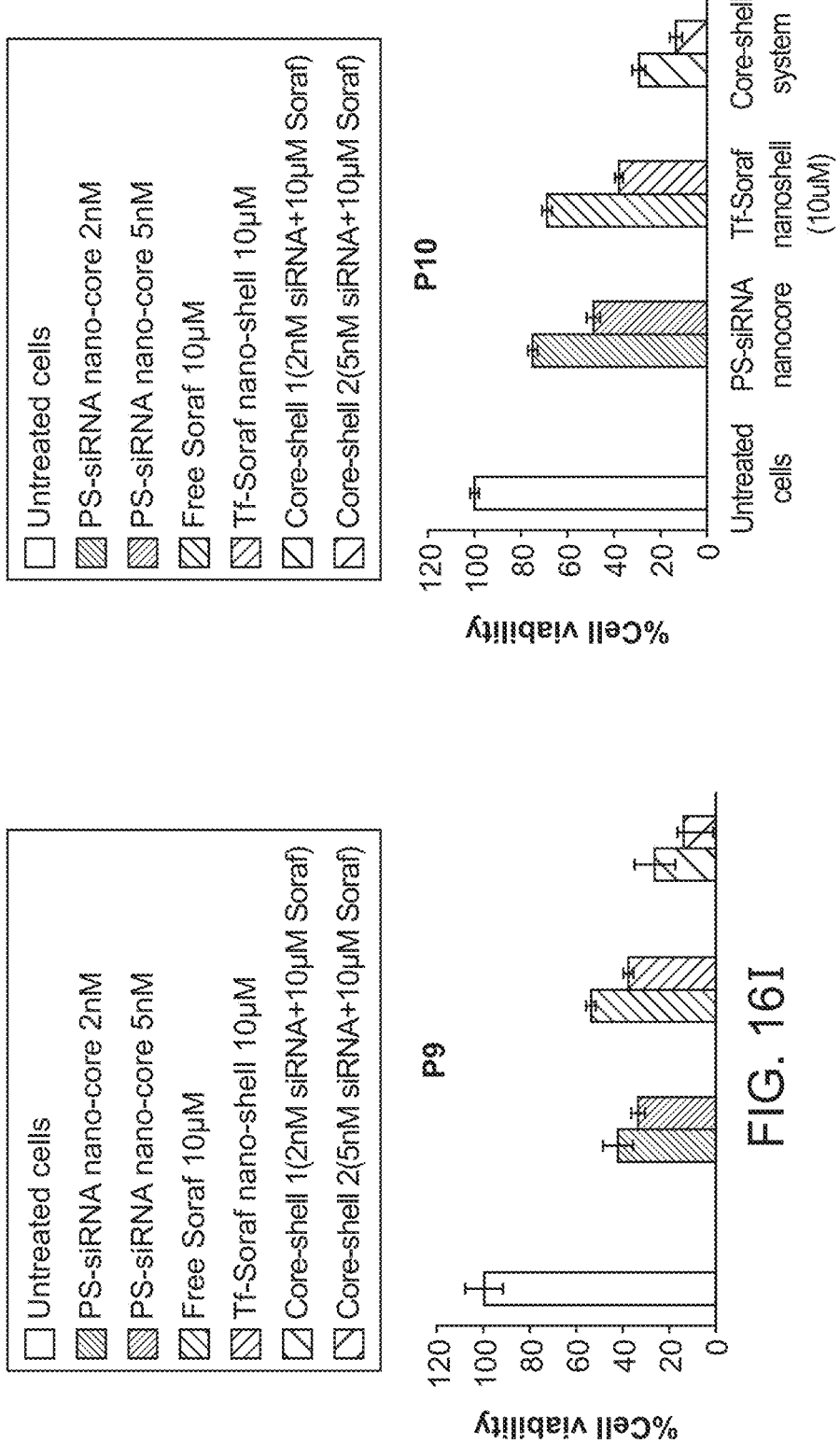

Results of Nanomedicine Treatment Against Chronic Myeloid Leukemia (CML):

The protamine siRNA-albumin sorafenib nanomedicine treated against immune disease such as chronic myeloid leukemia (CML) shows an example with the improved result in FIG. 14. The cytotoxic effect of (protamine-siRNA)-(transferrin-soraf) in drug resistant CML cells carrying amplification of BCR-ABL and STAT5 activation is shown in FIG. 14A. The normal healthy cells, which remain 100% viable upon treatment with (protamine-siRNA) and (transferrin-soraf) is shown in FIG. 14B.

Example-10

Genomic Level and Proteomic Level Effect of the Core-Shell Nanoparticles:

This example, as depicted in FIG. 15A-F shows genomic level effect of the protamine-siRNA nanocore in silencing the onco-gene, BCR-ABL, and protein (STAT5) inhibition effect of transferrin-Sorafenib nano-shell. FIG. 15A shows dose dependent cytotoxicity in K562 CML cells by nanocore at various concentrations and FIG. 15B shows the mechanism of toxicity as due to the silencing of BCR-ABL oncogene, which is further confirmed by immunoblot (FIG. 15C) where BCR-ABL onco-protein and its downstream signaling phosphorylated CRKL was found inhibited. On the other side, nano-shell exerted its enhanced effect of cytotoxicity compared (FIG. 15D) to free sorafenib through protein level inhibition of phospho-STAT5 and its downstream pathway Mcl-1 (FIGS. 15E and 15F). Clearly, this example demonstrates the independent molecular level activity of the constituents of the core-shell nanoparticles.

Example-11

Effect of Protamine siRNA-Albumin Sorafenib Nanomedicine in CML Patient Cells:

In this example we show the clinical significance of the core-shell nanoparticles by imparting synergistic cytotoxicity in actual patient samples, derived from n=14 CML patients. For this testing, we have isolated the blast population of leukemic cells from the patients at various stages of the disease and treated these cells in vitro with nano-core alone, nano-shell alone or nano-core-shells. As seen from the FIG. 16, all patient samples (P1-P14) showed enhanced cytotoxicity against core-shell NPs compared to core alone or shell alone. 10 μM concentration of sorafenib was used in nanoshell and 2 nm or 5 nm of siRNA against BCR-ABL was used in nanocore.

What is claimed is:

1. A core-shell particle formulation for delivering multiple therapeutic agents comprising:
   a protein core comprising protamine loaded with a first therapeutic agent; and
   a protein shell encapsulating the core to form a particle formulation, wherein the protein shell comprises cross-linked serum albumin loaded with a second therapeutic agent;
   wherein the first therapeutic agent of the core comprise siRNA and the second therapeutic agent of the shell comprise sorafenib;
   wherein the particle is configured to independently release the therapeutic agents from the core and the shell; and
   wherein the therapeutic agents are configured to be delivered by active targeting by conjugating the core-shell formulation with transferrin.

2. The formulation of claim 1, wherein the size of the core-shell particle is 1-1000 nm.

3. The formulation of claim 1, wherein the core or the shell further comprise lactoferrin, fibrinogen, gelatin, mucin, soy protein, apoferritin, ferritin, lectin, gluten, whey protein, prolamines, gliadin, hordein, secalin, zein, or avenin.

4. The formulation of claim 1, wherein the core or shell is further loaded with small molecule kinase inhibitors, phytochemicals, deoxyribozymes, ribozymes, shRNA, DNA, PNAs, or miRNAs.

5. The formulation of claim 1, wherein the core or shell is further loaded with demethylation agents, retinoids, antimetabolites, antimicrotubule agents, anti-angiogenesis agents, alkylating agents, biologic response modifiers, antitumor antibiotics, proteasome inhibitors, topoisomerase I inhibitors, hormones, immunomodulators, monoclonal antibodies, aromatase inhibitors, glucocorticosteroids, cytokines, enzymes, anti-androgen molecules, epigenetic modifiers, imatinib, nilotinib, erlotinib, gefitinib, dasatinib, or everolimus.

6. The formulation of claim 1, wherein the core or the shell or both are embedded with metallic nanoclusters comprising one or more of gold, silver, platinum, copper, or iron.

7. The formulation of claim 1, wherein the therapeutic agents are configured to be delivered from the shell and core sequentially.

8. The formulation of claim 1, wherein the therapeutic agents are configured to be delivered from the shell and core simultaneously.

* * * * *